US009927943B2

(12) United States Patent
Gannon et al.

(10) Patent No.: US 9,927,943 B2
(45) Date of Patent: *Mar. 27, 2018

(54) INTEGRATING ACTION BOXES FOR INFUSION MANAGEMENT

(75) Inventors: Mary Gannon, Shawnee, KS (US); Amanda Buckley, Olathe, KS (US); Hannah Fiechtner, Overland Park, KS (US); Stephanie L. Rogers, Kansas City, MO (US)

(73) Assignee: Cerner Innovation, Inc., Kansas City, KS (US)

( * ) Notice: Subject to any disclaimer, the term of this patent is extended or adjusted under 35 U.S.C. 154(b) by 1171 days.

This patent is subject to a terminal disclaimer.

(21) Appl. No.: 12/890,326

(22) Filed: Sep. 24, 2010

(65) Prior Publication Data
US 2011/0119612 A1    May 19, 2011

Related U.S. Application Data

(63) Continuation-in-part of application No. 12/622,213, filed on Nov. 19, 2009, now Pat. No. 8,291,337.

(60) Provisional application No. 61/244,717, filed on Sep. 22, 2009.

(51) Int. Cl.
| G06F 17/30 | (2006.01) |
| G06F 3/048 | (2013.01) |
| G09B 7/00 | (2006.01) |
| G06Q 10/00 | (2012.01) |
| G06F 3/0481 | (2013.01) |
| A61M 5/14 | (2006.01) |
| G06F 19/00 | (2018.01) |

(52) U.S. Cl.
CPC ............. *G06F 3/0481* (2013.01); *A61M 5/14* (2013.01); *G06F 19/3418* (2013.01); *G06F 19/3468* (2013.01)

(58) Field of Classification Search
CPC ....... G06Q 50/22; G06Q 50/24; G06F 19/322
USPC ............................ 715/771, 764, 210; 705/2
See application file for complete search history.

(56) References Cited

U.S. PATENT DOCUMENTS

| 4,878,175 A | 10/1989 | Norden-Paul et al. |
| 5,208,907 A * | 5/1993 | Shelton et al. ............... 715/200 |
| 5,337,405 A | 8/1994 | Lindauer et al. |
| 5,590,259 A * | 12/1996 | Anderson et al. ............ 715/209 |
| 5,592,945 A * | 1/1997 | Fiedler .......................... 600/523 |
| 5,687,717 A | 11/1997 | Halpern et al. |

(Continued)

OTHER PUBLICATIONS

Office Action dated Nov. 28, 2011 for U.S. Appl. No. 12/622,183, 12 pages.

(Continued)

*Primary Examiner* — Jordany Nunez
(74) *Attorney, Agent, or Firm* — Shook, Hardy & Bacon L.L.P.

(57) ABSTRACT

Methods, computer systems and computer readable media for receiving data from infusion pumps in a healthcare setting and displaying the data on a user device are provided. Centralized clinician views are provided to enable clinician to provide additional information for infusion data within selected time ranges. Embodiments provide near real-time graphical displays of infusion data to clinicians on separate user devices. In addition, near real-time graphical displays of patient physiologic data is displayed simultaneously to a clinician along with the infusion data.

10 Claims, 24 Drawing Sheets

(56) References Cited

U.S. PATENT DOCUMENTS

| | | | |
|---|---|---|---|
| 5,758,095 A | 5/1998 | Albaum et al. | |
| 5,781,442 A | 7/1998 | Engleson et al. | |
| 5,984,893 A | 11/1999 | Ward et al. | |
| 6,047,259 A | 4/2000 | Campbell et al. | |
| 6,434,531 B1 | 8/2002 | Lancelot et al. | |
| 6,529,217 B1 | 3/2003 | Maguire, III et al. | |
| 6,988,241 B1* | 1/2006 | Guttman et al. | 715/220 |
| 7,644,375 B1 | 1/2010 | Anderson et al. | |
| 7,685,026 B1 | 3/2010 | McGrady et al. | |
| 7,716,072 B1 | 5/2010 | Green, Jr. et al. | |
| 7,879,020 B1 | 2/2011 | Salinas et al. | |
| 7,895,179 B2 | 2/2011 | Chan | |
| 7,925,305 B2 | 4/2011 | Honda | |
| 8,065,169 B1 | 11/2011 | Oldham et al. | |
| 8,204,692 B2 | 6/2012 | Arango et al. | |
| 8,219,615 B2 | 7/2012 | Arav | |
| 8,689,124 B2 | 4/2014 | Amacker | |
| 2003/0004758 A1 | 1/2003 | Luttrell | |
| 2003/0069759 A1 | 4/2003 | Smith | |
| 2003/0140044 A1 | 7/2003 | Mok et al. | |
| 2003/0140928 A1 | 7/2003 | Bui et al. | |
| 2003/0200117 A1* | 10/2003 | Manetta et al. | 705/2 |
| 2003/0208490 A1 | 11/2003 | Larrea et al. | |
| 2003/0236683 A1* | 12/2003 | Henderson et al. | 705/2 |
| 2004/0032426 A1 | 2/2004 | Rutledge et al. | |
| 2004/0088187 A1 | 5/2004 | Chudy et al. | |
| 2004/0143459 A1 | 7/2004 | Engleson et al. | |
| 2004/0167804 A1 | 8/2004 | Simpson et al. | |
| 2005/0004700 A1 | 1/2005 | DiMaggio | |
| 2005/0038332 A1 | 2/2005 | Saidara et al. | |
| 2005/0055242 A1* | 3/2005 | Bello et al. | 705/2 |
| 2005/0065817 A1 | 3/2005 | Mihai et al. | |
| 2005/0192705 A1 | 9/2005 | Pinney et al. | |
| 2005/0209880 A1 | 9/2005 | Drelicharz et al. | |
| 2005/0216310 A1 | 9/2005 | Clements et al. | |
| 2005/0261940 A1 | 11/2005 | Gay et al. | |
| 2006/0036945 A1* | 2/2006 | Radtke et al. | 715/708 |
| 2006/0049936 A1 | 3/2006 | Collins et al. | |
| 2006/0054092 A1 | 3/2006 | Valencia et al. | |
| 2006/0059019 A1 | 3/2006 | Komischke et al. | |
| 2006/0100746 A1 | 5/2006 | Leibner-Druska | |
| 2006/0116639 A1 | 6/2006 | Russell | |
| 2006/0122729 A1 | 6/2006 | Murphy et al. | |
| 2006/0185605 A1 | 8/2006 | Renz et al. | |
| 2006/0229557 A1 | 10/2006 | Fathallah et al. | |
| 2006/0253299 A1 | 11/2006 | Konishi et al. | |
| 2007/0214014 A1* | 9/2007 | Suwalski et al. | 705/3 |
| 2008/0004502 A1* | 1/2008 | Ash et al. | 600/300 |
| 2008/0126969 A1 | 5/2008 | Blomquist | |
| 2008/0195422 A1* | 8/2008 | Nessinger et al. | 705/3 |
| 2008/0244377 A1 | 10/2008 | Erwig et al. | |
| 2009/0025087 A1 | 1/2009 | Peirson, Jr. et al. | |
| 2009/0037223 A1 | 2/2009 | Green et al. | |
| 2009/0105550 A1 | 4/2009 | Rothman et al. | |
| 2009/0153058 A1 | 6/2009 | Feng et al. | |
| 2009/0177992 A1 | 7/2009 | Rubalcaba, Jr. et al. | |
| 2009/0287350 A1 | 11/2009 | Johnson et al. | |
| 2010/0042437 A1* | 2/2010 | Levy et al. | 705/3 |
| 2010/0094653 A1 | 4/2010 | Tribble et al. | |
| 2010/0131883 A1 | 5/2010 | Linthicum et al. | |
| 2010/0169120 A1 | 7/2010 | Herbst et al. | |
| 2010/0169121 A1 | 7/2010 | Herbst et al. | |
| 2010/0271218 A1 | 10/2010 | Hoag et al. | |
| 2010/0292645 A1 | 11/2010 | Hungerford et al. | |
| 2010/0305965 A1 | 12/2010 | Benjamin et al. | |
| 2011/0119612 A1 | 5/2011 | Gannon et al. | |
| 2011/0137134 A1 | 6/2011 | Hemmerling et al. | |
| 2012/0209619 A1 | 8/2012 | Knotts et al. | |
| 2013/0262463 A1 | 10/2013 | Chittar et al. | |
| 2014/0032501 A1 | 1/2014 | Dulaney et al. | |

OTHER PUBLICATIONS

Final Office Action dated Apr. 4, 2012 for U.S. Appl. No. 12/622,183, 11 pages.

Office Action dated Dec. 16, 2011 for U.S. Appl. No. 12/622,213, 14 pages.

Baxter Launches New Triple-Channel Intravenous Infusion Pump, Sep. 23, 1998, PR Newswire; New York, p. 1.

Notice of Allowance dated Mar. 15, 2012 for U.S. Appl. No. 12/622,213, 12 pages.

Krishnan, et al.; Design of Interoperability—Coupled Safe Infusion Therapy in a Telemetry Setting, May 20, 2009, IFMBE Proceedings (1433-9277), vol. 24.

Final Office Action dated Jan. 23, 2013 in U.S. Appl. No. 12/890,403, 17 pp.

Final Office Action dated Jan. 28, 2013 in U.S. Appl. No. 12/890,397, 17 pp.

Pre-Interview Communication dated Nov. 15, 2012 in U.S. Appl. No. 12/890,403, 4 pages.

Pre-Interview Communication dated Nov. 14, 2012 in U.S. Appl. No. 12/890,397, 4 pages.

Notice of Allowance dated Nov. 13, 2014 in U.S. Appl. No. 12/890,403, 9 pages.

Gao et al., Participatory user centered design techniques for a large scale ad-hoc health information system, 2007, 20 pages, dl.acm.org.

Non-Final Office Action dated Nov. 19, 2014 in U.S. Appl. No. 13/651,987, 11 pages.

Non-Final Office Action dated Dec. 1, 2014 in U.S. Appl. No. 12/890,397, 24 pages.

Final Office Action dated Mar. 23, 2015 in U.S. Appl. No. 13/651,987, 12 pages.

Final Office Action dated Jul. 6, 2015 in U.S. Appl. No. 12/890,397, 22 pages.

Notice of Allowance dated Mar. 1, 2016 in U.S. Appl. No. 13/651,987, 10 pages.

Non-Final Office Action dated Mar. 14, 2016 in U.S. Appl. No. 12/622,183, 16 pages.

Final Office Action dated Aug. 4, 2016 in U.S. Appl. No. 12/622,183, 22 pages.

Non-Final Office Action dated Feb. 9, 2017 in U.S. Appl. No. 12/622,183, 20 pages.

Final Office Action dated Jun. 15, 2017 in U.S. Appl. No. 12/622,183, 22 pages.

* cited by examiner

| PATIENT | ROOM | INGREDIENT | INFUS. TY. | TOTAL | RATE | INFUS. | REMAINING | TIME LEFT | DISPENSING S... |
|---|---|---|---|---|---|---|---|---|---|
| COOPER, R | 2154 | DOPAMINE | CONT. | 50ML | 24.75ML/HR | 44.33ML | 5.66 | < 14 MIN | DELIVERED [SET] |
| COOPER, R | 2152 | PROPOFOL | CONT. | 25ML | 24.3ML/HR | 18.53ML | 6.46 | < 16 MIN | DELIVERY IN... [SET] |
| ROSS, J | 2152 | NOREPINEPHRINE | CONT. | 16ML | 7.5ML/HR | 13.44ML | 2.55 | < 21 MIN | [SET] |
| COOPER, R | 2154 | NOREPINEPHRINE | CONT. | 8ML | 7.5ML/HR | 5.43ML | 2.56 | < 21 MIN | DISPENSED [SET] |
| COOPER, R | 2154 | INSULIN | CONT. | 2.85ML | 1.32ML/HR | 2.36ML | 6.48 | < 23 MIN | DISPENSING IN... [SET] |
| MITCHELL, H | 2147 | DOPAMINE | CONT. | 250ML | 36.75ML/HR | 65.79ML | 184.2 | 5 HR 1MIN | [SET] |
| JACKSON, L | 2153 | DOPAMINE | CONT. | 250ML | 26.25ML/HR | 47.04ML | 202.95 | 7HR 44MIN | [SET] |
| LESTER, R | 2151 | DOPAMINE | CONT. | 250ML | 23.34ML/HR | 41.84ML | 208.15 | 8HR 56MIN | [SET] |
| WALKER, T | 2152 | DOPAMINE | CONT. | 250ML | 20.25ML/HR | 36.28ML | 213.71 | 10HR 34MIN | [SET] |
| ROBINSON, C | 2154 | PROPOFOL | CONT. | 500ML | 39.6ML/HR | 70.95ML | 429.04 | 10HR 51MIN | [SET] |
| FRYER, T | 2145 | PROPOFOL | CONT. | 500ML | 35ML/HR | 62.75ML | 437.24 | 12HR 30MIN | [SET] |
| FRYER, T | 2145 | MILRINONE | CONT. | 40ML | 2ML/HR | 62.75ML | 36.41 | 18HR 13MIN | [SET] |
| MORRIS, K | 2146 | DOPAMINE | CONT. | 250ML | 10.5ML/HR | 18.82ML | 231.17 | 22HR 2MIN | [SET] |
| ROBINSON, C | 2154 | MILRINONE | CONT. | 200ML | 6.6ML/HR | 11.83ML | 188.16 | 28HR 31MIN | [SET] |
| LESTER, R | 2151 | NOREPINEPHRINE | CONT. | 250ML | 7.5ML/HR | 13.44ML | 236.55 | 31HR 33MIN | [SET] |
| MARSHALL, B | 2156 | NOREPINEPHRINE | CONT. | 250ML | 7.5ML/HR | 13.43ML | 236.56 | 31HR 33MIN | [SET] |
| JONES, T | 2155 | MILRINONE | CONT. | 200ML | 4.88ML/HR | 8.74ML | 191.25 | 39HR 12MIN | [SET] |
| MORRIS, K | 2146 | MILRINONE | CONT. | 200ML | 4.2ML/HR | 7.53ML | 192.46 | 45HR 50MIN | [SET] |
| KIRKHOFF, B | 2150 | MILRINONE | CONT. | 200ML | 4.13ML/HR | 7.39ML | 192.6 | 46HR 39MIN | [SET] |
| FRYER, T | 2145 | INSULIN | CONT. | 100ML | 2ML/HR | 3.58ML | 96.41 | 48HR 13MIN | DISPENSING IN... [SET] |

| 11:00-13:00 | 14:00-16:00 |
|---|---|
| 36-36.3 | 36-37.2 |
| 73-75 | 75BMP1-72 |
| 22-23 | 20-22 |
| 98/60-99/60 | 96/60-99/60 |
| 73-77 | 73-76 |
| 99/60-99/60 | 96/60-99/60 |
| 73-74 | 73-74 |
| 91-93 | 91-94 |
| 5-5 | 7-7 |
| 10-10 | 8-10 |
| 5.0-5.5 | 5.0-5.5 |
| 2.8-2.9 | 2.7-2.7 |
| 8-10 | 10-10 |
| 82-84 | 84-86 |
| 10-10 | 5-10 |
| 17-17 | 10-17 |
| 17-17 | 10-17 |
| 10-10 | 10-10 |
| 5-5 | 10 | 5 |-10| 5 |
| 4-10 | 5-10 |
| 14-20 | 15-20 |
| 14-20 | 15-20 |
| 100-100 | 100-100 |
| 100-100 | 100-100 |
| 60-65 | 60-65 |
| 60-65 | 60-65 |
| 2-2 | 2-2 |
| 2-2 | 2-2 |

1600

| 11:00-13:00 | 14:00-16:00 |
|---|---|
| [36-36.3] | [36-37.2] |
| [73-75] | [75BMP1-72] |
| [22-23] | [20-22] |
| [98/60-99/60] | [96/60-99/60] |
| [73-77] | [73-76] |
| [99/60-99/60] | [96/60-99/60] |
| [73-74] | [73-74] |
| [91-93] | [91-94] |
| [5-5] | [7-7] |
| [10-10] | [8-10] |
| [5.0-5.5] | [5.0-5.5] |
| [2.8-2.9] | [2.7-2.7] |
| [8-10] | [10-10] |
| [82-84] | [84-86] |
| [10-10] | [5-10] |
| [17-17] | [10-17] |
| [17-17] | [10-17] |
| [10-10] | [10-10] |
| [5-5] | 10 | 5 |-10| 5 |
| [4-10] | [5-10] |
| [14-20] | [15-20] |
| [14-20] | [15-20] |
| [100-100] | [100-100] |
| [100-100] | [100-100] |
| [60-65] | [60-65] |
| [60-65] | [60-65] |
| [2-2] | [2-2] |
| [2-2] | [2-2] |

1610

| 11:00-13:00 | 14:00-16:00 |
|---|---|
| 36.3 | 36 |
| 75 | 75 BMP1 |
| 22 | 20 |
| 99/60 | 96/60 |
| 73 | 73 |
| 99/60 | 96/60 |
| 73 | 73 |
| 91 | 91 |
| 5 | 7 |
| 10 | 8 |
| 5.0 | 5.0 |
| 2.8 | 2.7 |
| 8 | 10 |
| 82 | 84 |
| 10 | 5 |
| 17 | 10 |
| 17 | 10 |
| 10 | 10 |
| 5 | 10 | 5 |
| 4 | 5 |
| 14 | 15 |
| 14 | 15 |
| 100 | 100 |
| 100 | 100 |
| 65 | 60 |
| 65 | 60 |
| 2 | 2 |
| 2 | 2 |

INTEGRATING ACTION BOXES FOR INFUSION MANAGEMENT

CROSS REFERENCE TO RELATED APPLICATIONS

This application is a continuation-in-part of U.S. patent application Ser. No. 12/622,213, filed on Nov. 19, 2009, and claiming the benefit of priority to U.S. Provisional Application Ser. No. 61/244,717, filed on Sep. 22, 2009, the entireties of which are hereby incorporated by reference. This application is related to commonly assigned U.S. patent applications entitled "Integrating Quick Sign for Infusion Management" 12/890,387 and "Integrating Protocols for Infusion Management" 12/890,403 filed concurrently herewith on the same date.

BACKGROUND

Infusion pumps infuse fluids, medications and/or nutrients into the circulatory system of an individual or patient. The infusions may be intravenous, subcutaneous, arterial, epidural and the like. Infusion pumps can administer injections continuously, intermittently, or upon patient request. Infusion pumps are used by clinicians for patients when more accuracy is needed than with manually adjusted gravitational administration of fluids into a patient's circulatory system. Infusions pumps can be used for infusion of a variety of fluids and medications including, but not limited to anesthesia, chemotherapy, IV drugs, blood transfusions and the like.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

One embodiment of the present invention is directed to one or more computer storage media having computer-executable instructions embodied thereon, that, when executed perform a method for indicating an action is required for an item associated with infusion documentation. Continuous data is received from at least one device operable to assist in treating a patient. A selected time range having multiple items is received from a user interface containing data from the continuous data feed. Items within the selected time range that require additional information from a clinician are displayed.

In another embodiment of the present invention, a graphical user interface (GUI) is stored on one or more computer-readable media and executable by a computing device. The GUI comprises a first display area configured for displaying data from a continuous data feed from at least one device. The GUI further comprises a second display area configured for receiving a selected time range associated with the data. The GUI further comprises a third display area configured for displaying items that require additional information from a clinician within the selected time range. The GUI further comprises a fourth display area configured for displaying an action box for entering additional information. The first, second, third, and fourth display areas are displayed simultaneously on a computing device of a clinician that is separate from the at least one device.

In yet another embodiment of the present invention, a computerized system for entering additional information associated with infusions documentation comprises a server comprising at least one component and operable to receive data transmitted by at least one device. A device information receiving component receives a continuous stream of data from the at least one device associated with a patient. A time range associated with the data is received by a time range selection component. An analyzing component determines more than one item of data requires additional information within the selected time range. Additional information is entered in an action box for the more than one item that is displayed by an action component.

BRIEF DESCRIPTION OF THE DRAWINGS

Embodiments are described in detail below with reference to the attached drawing figures, wherein:

FIGS. 7-12 are screenshots of graphical user interfaces in accordance with embodiments of the present invention;

FIG. 14 is a screenshot of a graphical user interface in accordance with an embodiment of the present invention;

FIGS. 15, 16, and 17 are screenshots of graphical user interfaces in accordance with embodiments of the present invention;

FIGS. 19-21 are screenshots of graphical user interfaces in accordance with embodiments of the present invention;

FIGS. 23-24 are screenshots of graphical user interfaces in accordance with embodiments of the present invention.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" might be used herein to connote different elements of methods employed, the terms should not be interpreted as implying any particular order among or between various steps herein disclosed unless and except when the order of individual steps is explicitly stated.

Embodiments of the present invention are directed methods, computer systems and computer readable media for receiving data from infusion pumps in a healthcare setting and displaying the data on a user device. Centralized clinician views are provided to manage individual and multiple patient infusions. Embodiments provide near real-time graphical displays of infusion data to clinicians on separate user devices. In addition, near real-time graphical displays of patient physiologic data is displayed simultaneously to a clinician along with the infusion data. This allows for clinician verification of the infusion data received to be completed within context of the patient's hemodynamic and vital sign documentation.

Embodiments of the present invention enable clinician to select protocols, presenting and recording data relevant to a treatment a patient is receiving. A user interface is operable for selecting multiple items that can be signed or edited with additional information, as necessary.

Embodiments of the present invention remove a clinician, such as nurse, from being the integrator of devices and data. Pro-active infusion volume status and alerts are provided in near real-time to both clinicians and pharmacists increasing nursing and pharmacy efficiency.

Figure 1:
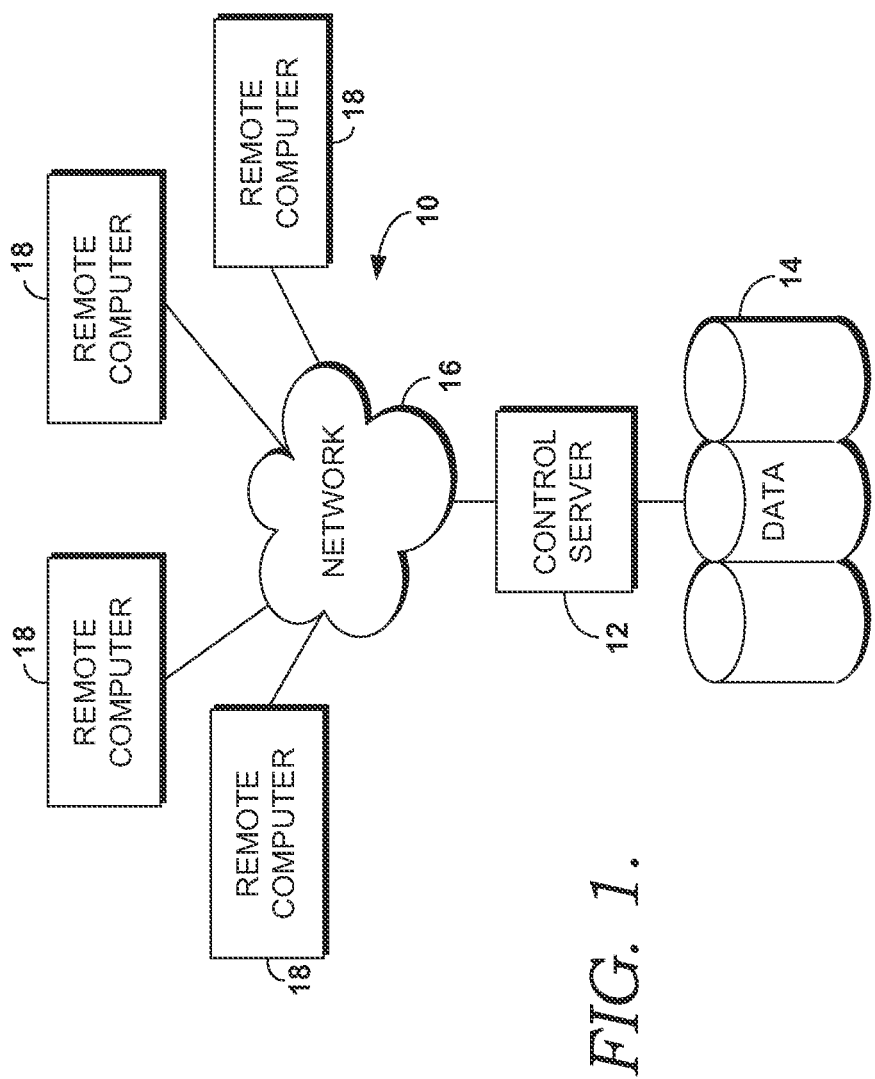
FIG. 1 is a block diagram of an exemplary computing environment suitable to implement embodiments of the present invention.

Having briefly described embodiments of the present invention, an exemplary operating environment suitable for use in implementing embodiments of the present invention is described below. Referring to FIG. 1 an exemplary computing environment (e.g., medical-information computing-system environment) with which embodiments of the present invention may be implemented is illustrated and designated generally as reference numeral 20. The computing environment 20 is merely an example of one suitable computing environment and is not intended to suggest any limitation as to the scope of use or functionality of the invention. Neither should the computing environment 20 be interpreted as having any dependency or requirement relating to any single component or combination of components illustrated therein.

The present invention might be operational with numerous other general purpose or special purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules include routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 20 includes a general purpose computing device in the form of a control server 22. Exemplary components of the control server 22 include a processing unit, internal system memory, and a suitable system bus for coupling various system components, including database cluster 24, with the control server 22. The system bus might be any of several types of bus structures, including a memory bus or memory controller, a peripheral bus, and a local bus, using any of a variety of bus architectures. Exemplary architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 22 typically includes therein, or has access to, a variety of computer-readable media, for instance, database cluster 24. Computer-readable media can be any available media that might be accessed by server 22, and includes volatile and nonvolatile media, as well as, removable and nonremovable media. Computer-readable media might include computer storage media. Computer storage media includes volatile and nonvolatile media, as well as, removable and nonremovable media implemented in any method or technology for storage of information, such as computer-readable instructions, data structures, program modules, or other data. In this regard, computer storage media might include RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 22. Combinations of any of the above also may be included within the scope of computer-readable media.

The computer storage media discussed above and illustrated in FIG. 1, including database cluster 24, provide storage of computer-readable instructions, data structures, program modules, and other data for the control server 22.

The control server 22 might operate in a computer network 26 using logical connections to one or more remote computers 28. Remote computers 28 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians might include a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 28 might also be physically located in nontraditional medical care environments so that the entire healthcare community might be capable of integration on the network. The remote computers 28 might be personal computers, servers, routers, network PCs, peer devices, other common network nodes, or the like and might include some or all of the elements described above in relation to the control server 22. The devices can be personal digital assistants or other like devices.

Exemplary computer networks 26 include local area networks (LANs) and/or wide area networks (WANs). Such networking environments are commonplace in offices, enterprise-wide computer networks, intranets, and the Internet. When utilized in a WAN networking environment, the control server 22 might include a modem or other means for establishing communications over the WAN, such as the Internet. In a networked environment, program modules or portions thereof might be stored in association with the control server 22, the database cluster 24, or any of the remote computers 28. For example, various application programs may reside on the memory associated with any one or more of the remote computers 28. It will be appreciated by those of ordinary skill in the art that the network connections shown are exemplary and other means of establishing a communications link between the computers (e.g., control server 22 and remote computers 28) might be utilized.

In operation, a clinician might enter commands and information into the control server 22 or convey the commands and information to the control server 22 via one or more of the remote computers 28 through input devices, such as a keyboard, a pointing device (commonly referred to as a mouse), a trackball, or a touch pad. Other input devices include microphones, satellite dishes, scanners, or the like. Commands and information might also be sent directly from a remote healthcare device to the control server 22. In addition to a monitor, the control server 22 and/or remote computers 28 might include other peripheral output devices, such as speakers and a printer.

Although many other internal components of the control server 22 and the remote computers 28 are not shown, those of ordinary skill in the art will appreciate that such components and their interconnection are well known. Accordingly, additional details concerning the internal construction of the control server 22 and the remote computers 28 are not further disclosed herein.

Figure 2:
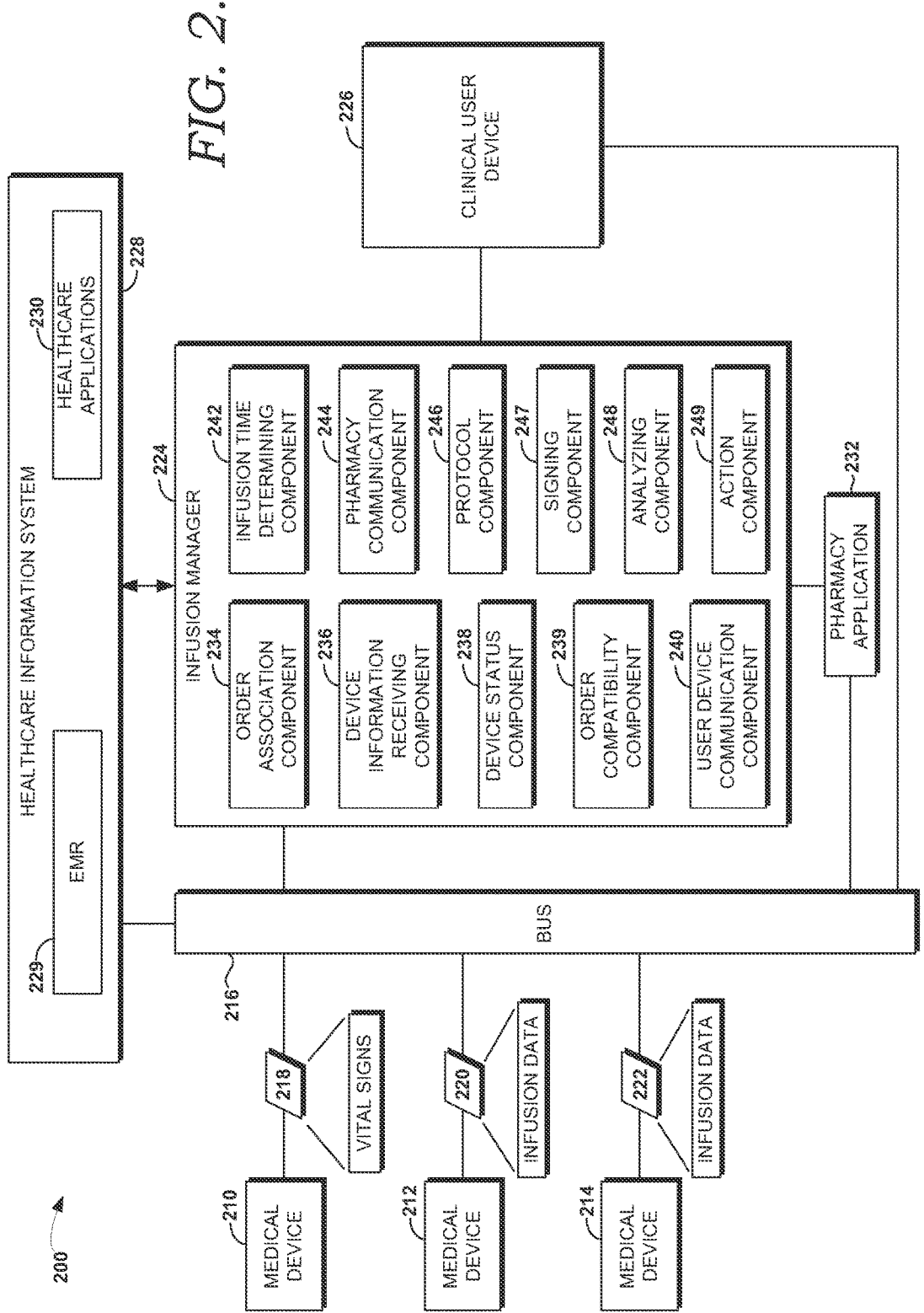
FIG. 2 is an exemplary system architecture suitable to implement embodiments of the present FIGS. 3-6 each include a flow diagram of a method in accordance with an embodiment of the present invention.

Turning now to FIG. 2, a schematic diagram depicts an operating environment, identified generally by reference numeral 200, suitable to practice an embodiment of the present invention. FIG. 2 includes various components that communicate with one another, including medical device 210, infusion pump devices 212 and 214, communication devices 226, bus 216, infusion manager 224, healthcare information system 228 and pharmacy application 232. In one embodiment of the present invention, data generated by a medical device 210 or an infusion pump device 212, and 214 is routed to and managed by infusion manager 224, as opposed to, each medical device 210 and infusion pump device 212 displaying information on the medical device or infusion pump respectively. For example, data 218, 220, and 222 is communicated to bus 216, which might then forward the data to infusion manager 224 to be further processed and routed. Before describing in more detail how these components communicate, each component will be generally described.

In an embodiment of the present invention, medical device 210 might include cardiac monitors, ventilators, balloon pumps, patient beds, sequential-compression devices, electronic security devices, and vital-sign detecting devices. Medical device 210 may generate various data (e.g., measured heart rate) that, as described in more detail below, is communicated to other components (e.g., bus 216) of operating environment 200. Moreover, medical device 210 might also receive information from components of operating environment 200.

In another embodiment of the present invention infusion pumps 212 and 214 infuse fluids, medications and/or nutrients into the circulatory system of an individual or patient. The infusions may be, but are not limited to, intravenous, subcutaneous, arterial, epidural and the like. Infusion pumps can administer injections continuously, intermittently, or upon patient request. Infusion pumps are used by clinicians for patients when more accuracy is needed than with manually adjusted gravitational administration of fluids into a patient's circulatory system. Infusions pumps can be used for infusion of a variety of fluids and medications including, but not limited to anesthesia, chemotherapy, IV drugs, blood transfusions and the like. The fluid, medication and/or nutrients are typically contained in an infusion container, such as an infusion bag. It will be appreciate that any type container may be utilized to hold the infusion fluid, medication and/or nutrients. Infusion pumps 212 and 214 generate various data, including, but not limited to, remaining volume of infusion (e.g., amount remaining in fluid container), rate of infusion (e.g., how fast fluid is being infused), alerts (e.g., air in line, maintenance of pump needed, high backpressure, low infusion, occlusion, or pump stopped). This data is communicated to other components (e.g., bus 216) of operating environment 200. Moreover, infusion pumps 212 and 214 might also receive information from components of operating environment 200.

Healthcare information system 228 includes an integrated system of healthcare-related information that is usable by a healthcare facility to operate and provide patient care. For example, healthcare information system 228 includes an electronic medical record 229 (also referred to herein as "EMR") and a healthcare applications component 230. EMR 229 includes an electronic version of patient records including information for the patient, such as medication and infusion orders, tasks, images, examination reports, testing and lab results, medical history, etc. Healthcare applications component 230 includes information that is input and provided at a patient's point-of-care (e.g., patient bedside) to assist healthcare professionals to provide appropriate care. An exemplary applications component 230 includes a patient order entry component for entering electronic healthcare orders for a patient. In an embodiment of the present invention, healthcare information system 228 receives information from other components, as will be described in more detail below. Moreover, healthcare information system 228 might also provide information that is communicated to other components of operating environment 200.

Communication devices 226 include devices that are used within a healthcare facility to receive, display and send information to a user, such as a clinician. Communication devices 226 also facilitate requests to receive additional information. Exemplary communication devices 226 include personal communication devices, a clinician computer workstation, and an email system. Personal communication devices include devices that are used by an individual to receive and send information, such as an in-house phone, a pager, and a mobile device. Workstations include a remote computer terminal that is used to present information to a user, such as a clinician, and receive input. Workstations might be set up at a nurse's station to or at a patient bedside. Accordingly, in an embodiment of the present invention, communication devices 226 present to users information that is received from other components of operating environment 200. Moreover, communication devices 226 might also receive inputs from a clinician that are communicated to other components of operating environment 200. Communication devices 226 also communicate to other components of operating environment 200 requests to receive additional information. For example, personal communication device 246 might communicate information to infusion manager 224, HIS, 228 EMR 229, pharmacy application 232 and medical devices 210, 212 and 214.

Pharmacy application 232 is an electronic application for receiving medication orders, such as infusion orders, to be filled. An exemplary pharmacy system is Cerner Millennium Pharmnet by Cerner Corporation, Kansas City Mo. Typically orders for medications, fluids and nutrients to be filled by a pharmacist are displayed in the pharmacy or pharmacy IV room. The pharmacist can use this information to drive the pharmacy workflow and make sure the necessary medication orders are filled. In another embodiment, pharmacy application 232 may be an automated pharmacy dispensing system such as Cerner RXStation by Cerner Corporation of Kansas City, Mo. The automated pharmacy system may be an apparatus pre-loaded with medication, fluids and/or nutrients that may be dispensed to fill patient orders.

As previously indicated, and as depicted in FIG. 2, each of medical devices 210, infusion pumps 212 and 214, healthcare information system 228, communication devices 226 and pharmacy application 216 may be in communication with bus 216. Bus 216 generally provides a connection framework for these components by creating and managing all connections, providing a messaging architecture to facilitate an exchange of information between the various components of FIG. 2, and providing general operational and management capabilities for connected devices. In one embodiment, medical device 210, infusion pumps 212 and 214, communication devices 226, healthcare information system 228 and pharmacy application 232 communicate with bus 216 as described in U.S. patent application Ser. No. 12/347,475 (U.S. patent application Ser. No. '475), which is incorporated herein by reference. For example, infusion pumps 212 and 214 might include various different types of infusion pumps that are manufactured by various different vendors. As such, components of FIG. 2 might communicate with bus 216 via a gateway (e.g., device gateway or internal gateway), an adapter, or by any other means described by U.S. patent application Ser. No. '475. In a further embodiment, bus 216 includes those capabilities described in U.S. patent application Ser. No. '475. As indicated in U.S. patent application Ser. No. '475, once data is received (e.g., data 218, 220, 222, and 227) it can be sorted and routed to other applications.

In an embodiment of the present invention, such applications are included in an infusion manager 224. As such, bus 216 might receive information (e.g., data 218, 220, and 222) and route the data to infusion manager 224. Moreover, bus 216 might receive information from communication devices 226 and route the information to infusion manager 224. In a further embodiment, bus 216 receives information from healthcare information system 228 and routes the information to infusion manager 224. In another embodiment, bus 216 receives information from infusion manager 224 and routes the information to other components. For example, bus 216 routes information from clinician devices 226 to healthcare information system 228.

In an embodiment of the present invention, infusion manager 224 communicates with bus 216 and functions to consolidate and manage information received from the various components of operating environment 200. In this embodiment, instead of components communicating directly with one another, information is routed through and processed by infusion manager 224. Infusion manager 224 allows for consolidation and communication of information from various sources, which may not easily integrated or combinable by direct communication. For example, infusion manager 224 allows for information from infusion pumps 212 and 214 to be packaged with information from medical device 210, healthcare information system 228 and pharmacy application 232 in order to generate and communicate a more information-rich notification to a notification recipient (e.g., personal communication device 246). Moreover, a set of normalized information is more easily sorted and reported than a set of information that organized in alternative formats of various information sources. Alternatively, medical device 210, infusion pumps 212 and 214, pharmacy application 232, clinician user devices 226 and healthcare information system 228 may communicate directly with infusion manager via a network environment.

Infusion manager 224 communicates with bus 216 and functions to document, display and manage infusion information received from infusion pumps 212 and 214. Infusion manager includes order association component 234, device information receiving component 236, device status component 238, order compatibility component 239, user device communication component 240, infusion time determining component 242, and pharmacy communication component 244. While these components are included in the embodiment of FIG. 2, any number of components, either more or less than the illustrated components, may be used to accomplish the purposes of the present invention. Other components and subcomponents are contemplated to be within the scope of the present invention. Furthermore, although depicted as residing on one device, such as a server, it will be appreciated that any number of components and/or subcomponents may reside on any number of computing devices or servers.

Order association component 234 associates the infusion pump and/or pump channel for a patient and an order for a patient in response to receiving an indication that the infusion pump and patient order are to be associated. In one embodiment, if the infusion pump is a multi-channel infusion pump, an order for a patient may be associated with the pump and the particular channel utilized for administration of the ordered medication, fluid and/or nutrient. For example, a first order for a first medication is associated with first channel of a multi-channel pump and a second order for a second, and different, medication for the same patient associated with a second channel of a multi-channel pump.

In one embodiment, identifications of the patient, infusion pump and channel are received. The identifications may be received in a number of ways, including, but not limited to, scanning a barcode associated with the patient, pump and/or channel, entering a name or identification associated with the patient, pump and/or channel or searching an electronically searchable database for a patient, pump and/or channel.

Figure 7:
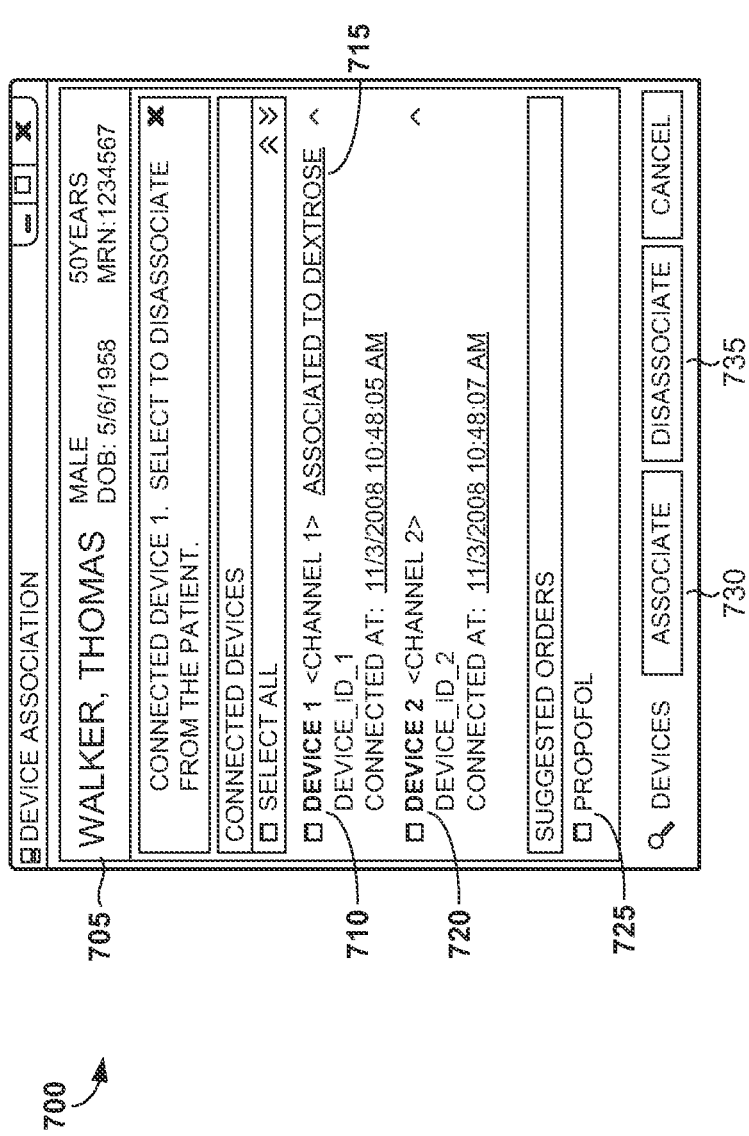

This indication to associate an infusion pump and/or channel and patient order may take many forms. An order is an instruction or request for a procedure, a medication, infusion fluid, nutrients, a laboratory test, an evaluation, a treatment, or a nursing task to be performed for a patient. An explicit association may be available to the user, such as through a selectable button on a graphical user interface displayed on the user device as shown in FIG. 7, described in more detail below. The patient order, infusion pump and/or channel may be associated prior to, simultaneously with of after receiving data from an infusion pump and/or channel. Order association component 234 may suggest orders to associate with one or more infusion pumps and/or channels. For example, order association component 234 may filter patient orders to display only orders to be administered by infusion pump as shown in FIG. 7 which will be discussed in further detail below.

Device information receiving component 236 acquires or receives data from an infusion pump and associated channel that has been associated with a patient and/or order for the patient. The type of data that may be received information regarding volume of fluid infused, volume of fluid remaining to be infused, rate of infusion and alerts. Device information receiving component 236 may also receive data from medical devices other than infusion pumps, such as vital sign and blood pressure monitors. The data is in computerized form and is communicated in electronic form to the BUS and/or event manager without any user intervention. For example, the device would automatically be sent to the BUS and/or infusion manager without a user, such as a nurse or clinician, having to manually key-in or enter any information into a computer system.

In one embodiment, the data received from the infusion pumps and medical devices can be manipulated (e.g., by a clinician) prior to being stored in the patient's EMR. The data may be stored in an application or service such that a user can edit the data prior to the data being transmitted to the patient's EMR. Device information receiving component 236 continually receives data from the associated infusion pumps and medical devices as long as they are associated to the patient and/or patient's order. A continuous feed of data may be fed from the infusion pump and/or medical device to bus 216 and then to infusion manager 224.

Device status determination component 238 determines the status of the device based on data received from an infusion pump. The status may include whether or not a device is connected to the system or if it has lost connectivity, whether a pump is infusing or has been stopped, volume of fluid remaining to be dispensed, rate of infusion and maintenance information. In one embodiment, if the infusion manager 224 does not receive any data from an infusion pump (e.g., such as a heartbeat signal of the device or any other data) it will be determined that the infusion pump has lost connectivity.

In another embodiment, infusion manager 224 may not receive any information about rate or volume remaining but still receives an indication given at a certain interval of time that a particular infusion pump is connected to bus 216. Based on this data, device status determination component 238 determines that the infusion has been stopped but the infusion pump is still connected. Device status determination component 238, if needed, also performs any necessary conversions on the data received from the infusion pump needed to determine the rate of infusion, volume remaining to be infused based on data received from an infusion pump or type of alert needed. In addition, device status determination component 238 can rate the alert information received from the infusion pump and determined by device status determination component 238 by level of severity. The level of severity may be represented by an icon displayed for the alert by user device communication component 240 discussed in further detail below.

Figure 9:
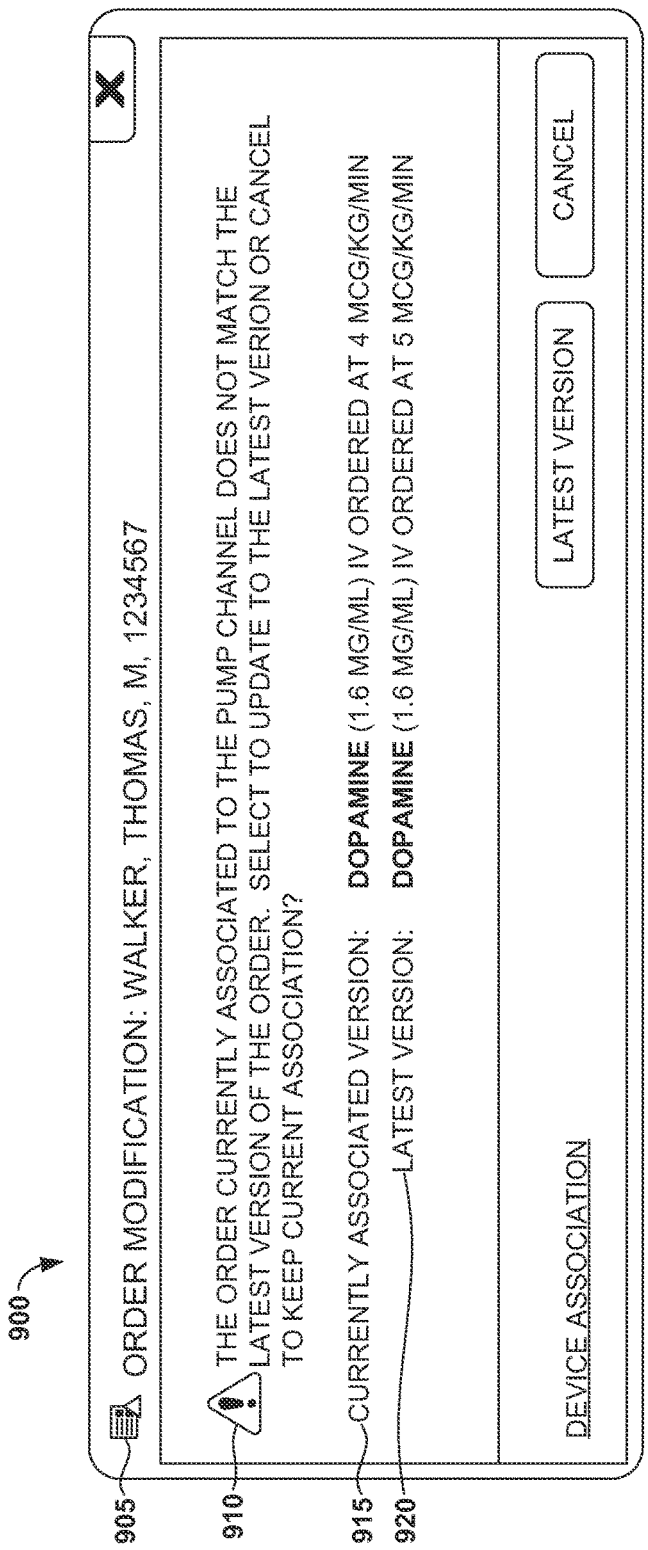

Order compatibility determining component 239 generates an alert that data received from an infusion pump and associated channel does not match the associated order. For example, if the rate of infusion for the associated pump and/or channel received from the data from the pump does not match the rate of the associated order, order compatibility determination component 239 generates an alert notifying a clinician of the discrepancy. In addition, order compatibility determining component 239 can access current electronic orders to be administered by infusion pump for the patient and suggest a more recent version of an order or the closest order that may fit the data being received by the infusion pump as depicted in FIG. 9, which will be discussed in more detail below.

User device communication component 240 displays and communicates data to the user devices 226 and can receive user inputs from a user device 226. The user devices 226 are separate devices from the medical device 210 and infusion pumps 212 and 214. User device communication component 240 can display a variety of information received from an infusion pump in a variety of formats. User device communication component 240 displays an identification of a medical device an associated order for a patient. In addition, user device communication component 240 may display available infusion pumps, pump channels and patient orders to be associated by the order association component 234.

Textual information regarding the rate of infusion of the infusion pump, the volume infused and the volume remaining to be infused may be displayed to a clinician. Textual information regarding the status of the infusion pump generated by device status determination component 238 may be displayed by user device communication component 240. Patient information from the patient's EMR includes details of the order associated with the infusion pump and/or channel, patient identification and demographic information. In addition, user device communication component 240 may provide data received from an infusion pump in a format such that it may be graphed against time on graphical user interface for display to a clinician.

Figure 8:
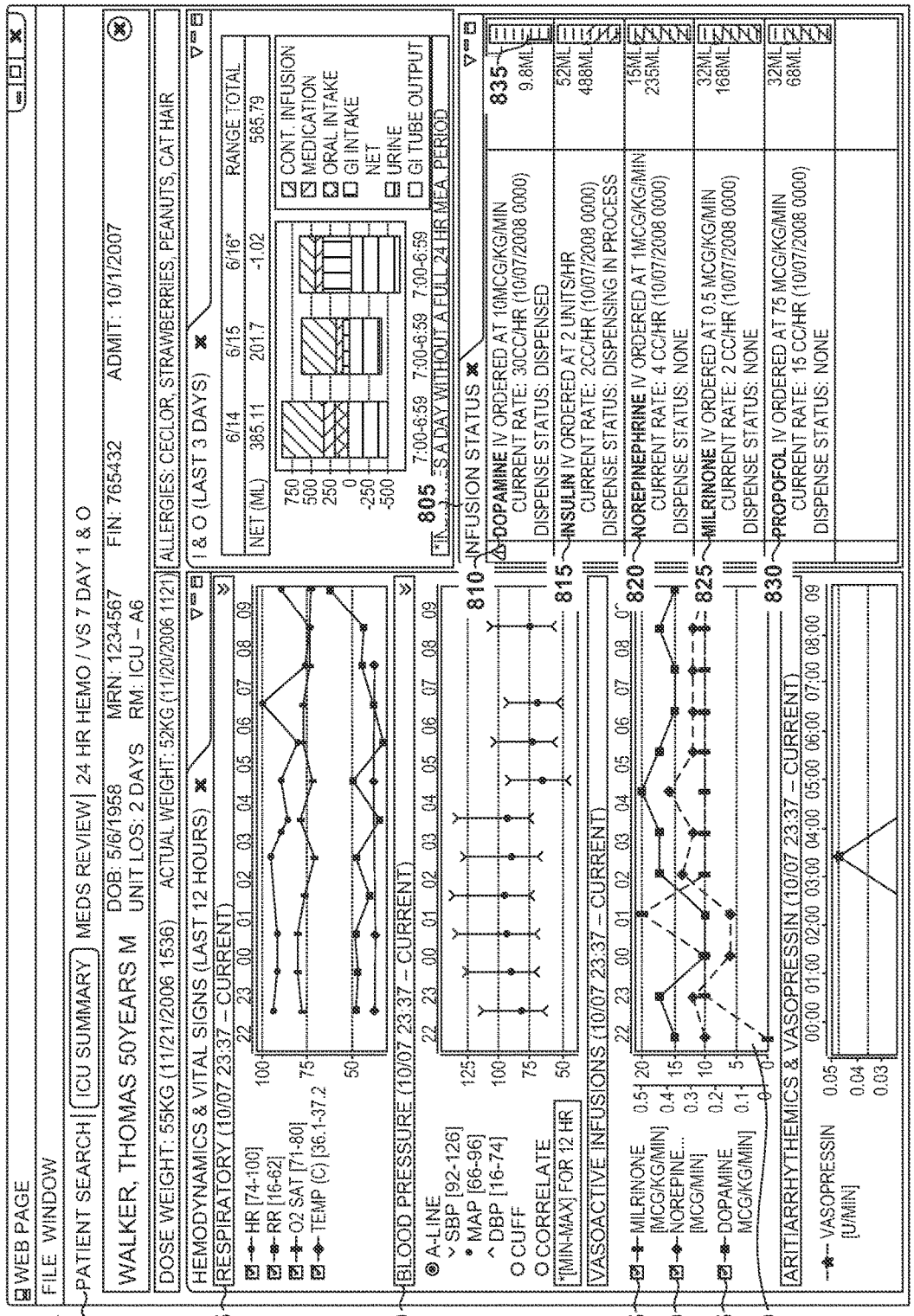
Figure 10:
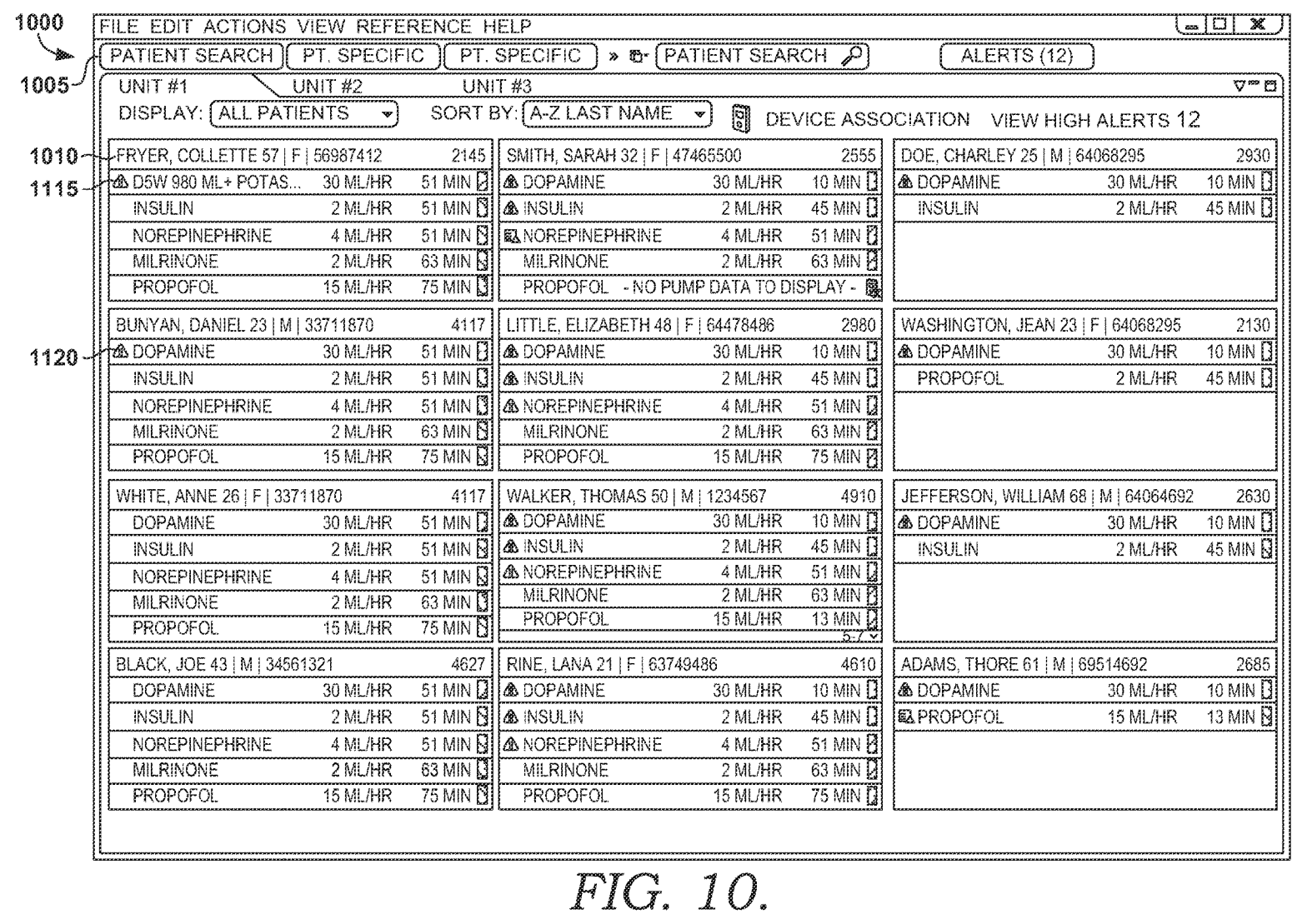

Alerts from the data received from the infusion pump may be displayed along with textual icon and/or color coding indicating the severity of the alert. For example, an alert indicating that there is air in the line for the infusion pump would be indicated as high severity, an alert that an infusion bag had low volume would be indicated as medium severity and a maintenance alert to calibrate the infusion pump would be indicated as low severity. Additional alerts, such as an alert generated by order compatibility determining component 239, alerting a clinician that the order associated with the infusion pump does not match the data being received from the infusion pump may also be displayed. User device communication component 240 may display infusion data for individual patients as shown in FIG. 8 described in more detail below or for multiple patients simultaneously as shown in FIG. 10 also described in more detail below.

User device communication component 240 also provides a user, such as a clinician, with the opportunity to review the data acquired from the infusion pump. The data acquired from the infusion pump and vital signs collected by other medical devices are displayed to the user in a format that allows the user to edit the data received from the infusion pump in context of the patient's vital signs, if desired. Alternatively, the user may authenticate the data as received from the medical device. Once the data received from the infusion pump has been reviewed by a clinician, and once the user has had the opportunity to edit or add any other information, the user may select a button, such as a sign button, that indicates that the data is ready to be transmitted or published to the patient's EMR.

Protocol component 246 provides a user, such as a clinician, with the opportunity to display and save data to a patient's EMR at an interval, in one embodiment, relevant to a treatment the patient is receiving. For example, a post-operative cardiothoracic surgery order may require monitoring vital signs at specific intervals, providing medications at varying doses through various methods of delivery, such as through an infusion pump, performing laboratory tests at specific times, or performing other actions or activities that are time dependent. Orders for post cardiac catheterization or post carotid arterial stent may have entirely different requirements. To illustrate, an abbreviated sample of two real-world orders are contrasted below to distinguish the requirements for vital signs:

Post-Operative Cardiothoracic Surgery Order
Vital Signs:
Record the following on arrival to ICU: MAP q 5 min×15 min, q 15 min until stable×2 hours, q 30 min×2 hours, q 1 hour, then decrease to q 2 hours when patient stable and prn:
Do Not Wedge Swan
Arterial pressure (from arterial line, record cuff pressure on admission and q shift)

Heart Rate
Respiratory Rate (spontaneous/mechanical)
MAP CVP (direct monitoring)
PA systolic/diastolic pressures $SaO_2$ Record the temperature on admission and then q 4 hours. Call physician for temperature>38.5 Celsius. Urine culture if indicated. Sputum culture and blood culture×2 q 30 minutes if temperature>38.5 Celsius.

Record urine volume every hour

Record cardiac output/index/SVR on admission, at 1 hour and every 4 hours postoperative (unless weaning vasoactive medication—then 30 minutes to 1 hour after change).

Call physician for:
MAP<60 mmHg or >100 mmHg
Low BP (MAP<60 or SBP<90)
CVP>18 mmHg
Heart rate<60 or >120 or rhythm change
$SaO_2$<95% (African-American) or <92% (Other)
Cardiac index<2.1 L/min/$m_2$
Urine output<0.5 mL/kg/hr
Chest tube drainage≥150 ml/hr
Post Cardiac Catheterization Order
Vital Signs:
Record the following: q 15 min×4, then q 30 min×4 then q 1 hr×4 then routine and prn
For Femoral Sites:
Examine procedural site for swelling/bleeding
Assess distal extremity for warmth, color, sensation, and presence of pulse with each vital sign
NOTIFY cardiologist for uncontrollable bleeding, hematoma, loss of pulse in affected extremity, SBP<80 mm or HR>110
For Brachial/Radial Caths:
Check right brachial/radial area for bleeding and radial pulse every 30 min×6
Keep arm straight for 1 hour
Check hand for pain, numbness, and capillary refill with each vital sign.

Orders for various treatments often span many pages and include items such as vital signs, general measures, extubation, medications, laboratory testing, among many others. In one embodiment, a protocol corresponds to the unique requirements evidenced by the order for a specific treatment. For example, a clinician may select, in one embodiment, a protocol corresponding to a post-operative cardiothoracic surgery order. In another embodiment, a clinician may select a protocol corresponding to a post carotid arterial stent order. In yet another embodiment, a clinician may select a protocol corresponding to a conscious sedation procedure. A clinician may select, in one embodiment, a protocol corresponding to a rapid sequence intubation procedure. In another embodiment, a clinician may select a protocol corresponding to a pacemaker insertion procedure. A clinician may select, in one embodiment, an acute myocardial infarction protocol. In another embodiment, a clinician may select a stroke protocol.

Figure 15:
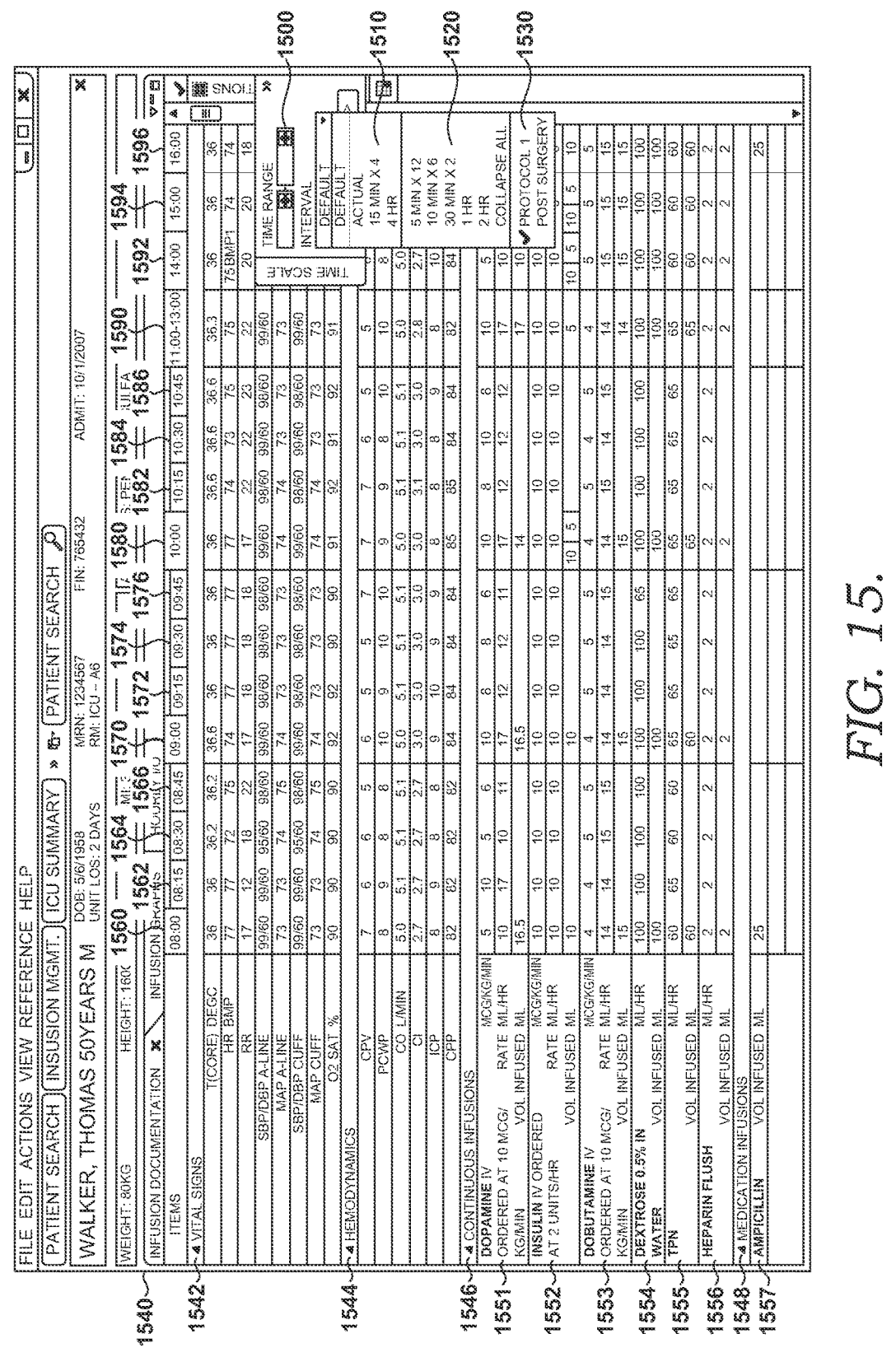

Referring back to FIG. 2, the user device communication component 240 displays available data to a clinician. Upon receiving an order for a patient, the clinician may desire to select the protocol corresponding to that order. The protocol component 246 presents the clinician with an interface that, in one embodiment, comprises a drop down box, shown in FIG. 15, allowing the clinician to select, from a list of available protocols, the desired protocol. In another embodiment, the protocols appear in order of most frequent use 1510.

By selecting a protocol via the protocol component, the protocol component communicates with the device information receiving component and the user device communication component, as necessary, such that the appropriate data is displayed and if desired, transmitted to the patient's EMR. This avoids the onerous and time-consuming task of requiring a clinician to manually collect and record data, or manually alter collection and recordation times. Accordingly, the clinician is able to spend more time caring for the patient and less time reviewing and fulfilling requirements associated with each individual patient's order.

Analyzing component 248 provides a user, such as a clinician, with the opportunity to review data displayed and recorded at various intervals for items that may require further clinician interaction. For example, in one embodiment, data may need to be reviewed and signed by a clinician. In this embodiment, control is passed to a signing component 247. The signing component, in one embodiment, allows a clinician to select multiple items that need to be signed, presents the clinician with a signing box, and allows the clinician to mark multiple items as signed so the data can be saved in the patient's EMR.

In another embodiment, the data may require that the clinician enter additional information prior to signing. For example, in various embodiments, additional information such as patient's weight, site of administration of medication, or a witness name may be required. In this embodiment, control is passed to an action component 249. The action component, in one embodiment, allows a clinician to select multiple items that require additional information, presents the clinician with an action box, and allows the clinician to edit multiple items with additional data as necessary so the data may be signed and saved in the patient's EMR.

Infusion time determining component 242 determines the time remaining until an infusion needs to be replaced and/or refilled. A variety of information may be utilized to determine the time remaining infusion fluid to be infused. The information utilized may include patient information (patient location, patient identifier), order information (type of infusion, amount, etc.), information from pump (rate, volume infused, volume remaining, alerts) and information from pharmacy that filed the current infusion (e.g., expiration of current infusion). Oftentimes infusion fluids, medications and nutrients have a set expiration time. This information can be obtained from the data from the pharmacy that filled the current infusion. For example, a 50 ml infusion of Dopamine may expire in 12 hours.

To calculate the estimated time remaining until the current infusion fluid runs out, infusion time determining component 242 receives the current rate associated from the infusion pump associated with the patient order or calculates average rate over a period of time (e.g., 24 hours) utilizing the rate data received from the infusion pump associated with the patient order. Additionally, infusion time determining component 242 receives the remaining volume from the infusion pump associated with the patient order. The infusion time determining component 242 then utilizes the rate and volume remaining to determine the estimated time remaining of the current infusion. For example, with reference to FIG. 13, the estimated time remaining for a continuous infusion of dopamine that has 5.66 ml remaining to be infused and a current or average infusion rate of 24.75 ml/hour is calculated as follows:

5.66 ml/24.75 ml/hour=0.228 hours 0.288 hours×60 minutes=13.72 minutes

As such, the estimated time remaining for the infusion is calculated as <14 minutes. In one embodiment, the infusion time determining component 242 compares the estimated time remaining (e.g., <14 minutes) to the expiration time of the current infusion. In this example, the infusion time determining component 242 determines that the estimated time remaining for the infusion will occur before the expiration time of the current infusion and such the estimated time remaining would remain <14 minutes. As such, the pharmacy communication component 244, discussed in more detail below, would notify the pharmacy application 232 that the estimated time remaining of the current infusion is <14 minutes as shown in FIG. 13.

In another embodiment, the infusion time determining component 242 determines that the current infusion will expire in <5 minutes. Thus, the current infusion will expire before the estimated time remaining in the infusion. Thus, pharmacy communication component 244 communicates to the pharmacy application 232 that the current infusion will expire in <5 minutes.

In addition, infusion time determining component 242 determines that the rate of infusion for a patient order is increasing or decreasing. Infusion time determining component 242 utilizes rate information received from an infusion pump over a period of time an average. The infusion time determining component 242 compares the average rate to the current rate to determine if the rate is increasing, decreasing or staying the same. An indication of the increase or decrease in rate can be displayed to a pharmacy application 244 by pharmacy communication component 232.

Figure 13:
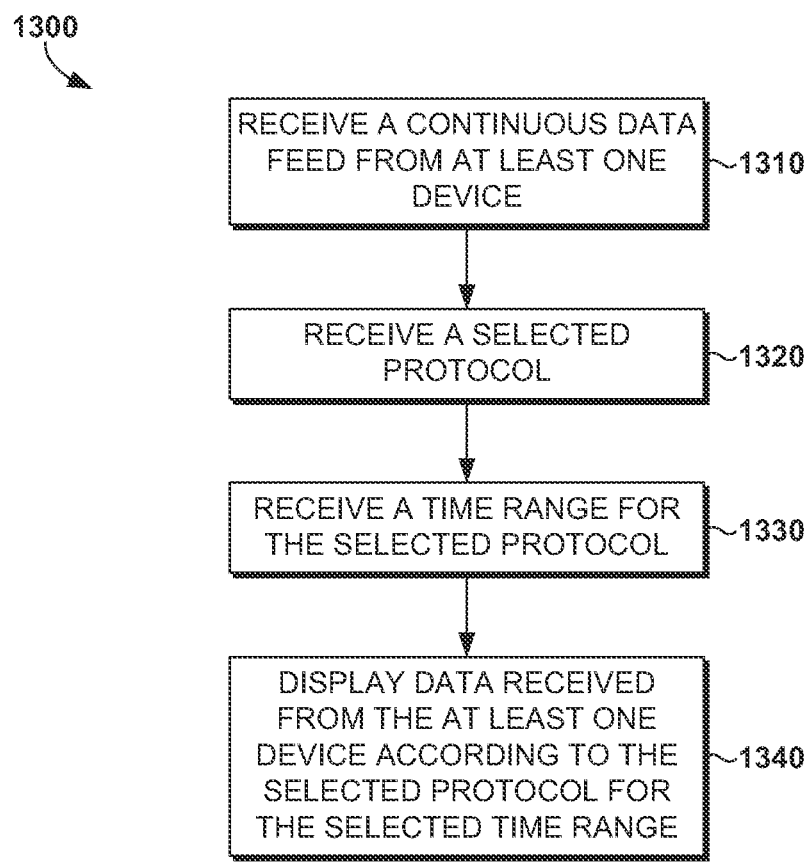
FIG. 13 is a flow diagram of a method in accordance with an embodiment of the present invention.

Infusion time determining component 242 may also filter infusion data for multiple patients to prioritize the pharmacy workflow as shown in FIG. 13. A variety of information may be utilized to prioritize the workflow in the pharmacy. The information utilized may include patient information (patient location, patient identifier), order information (type of infusion, amount, etc.), information from pump (rate, volume infused, volume remaining, alerts), information from pharmacy that filed the current infusion (e.g., expiration of current infusion), known preparation time to prepare an infusion and inventory information.

The infusion time determining component 242 first looks at the time remaining for a current infusion for a patient. For example, infusion time determining component 242 would rank the current infusion for a patient with the least amount of time remaining for the current infusion as the highest priority and a current infusion for the patient with the most amount time remaining the lowest priority. Infusion time determining component 242 would then determine if there is inventory on hand for a current patient infusion. If so, the infusion time determining component 242 may decrease the priority of replacing the current infusion as an infusion from the current inventory will just need to be delivered to the patient. Another factor that may be taken into account is the time to prepare a replacement infusion fluid. For example, a first patient has a current infusion that is estimated to run out in 14 minutes and a second patient has a current infusion that is estimated to run out in 25 minutes. However, the replacement infusion for the first patient will only take two minutes to prepare but the replacement infusion for the second patient will take 20 minutes to prepare. As such, the infusion time determining component 242 will determine to increase the priority of the replacement infusion for the second patient and will change the prioritization rankings accordingly.

Pharmacy communication component 244 displays and communicates infusion pump data to pharmacy application 232. Pharmacy communication component 244 provides near real-time pharmacy awareness of the infusion status of multiple infusion pumps within one or more healthcare facilities.

Pharmacy communication component 244 can display a variety of information received from an infusion pump in a variety of formats to a pharmacy, pharmacy user or an automated pharmacy dispensing system such as Cerner RXStation by Cerner Corporation of Kansas City, Mo. Pharmacy communication component 244 displays patient information such as patient name or ID number along with the patient's location obtained from the patient's EMR 229. Pharmacy communication component 244 displays details regarding the infusion order for the patient such as ingredient, infusion type, and volume to be infused. In addition, pharmacy communication component 244 also displays data received from infusion pumps 212 and 214 including rate of infusion, volume infused, remaining volume to be infused and alerts. Pharmacy communication component 244 also displays calculations performed by infusion time determining component 242 of time left before a current infusion fluid runs out.

Figure 3:
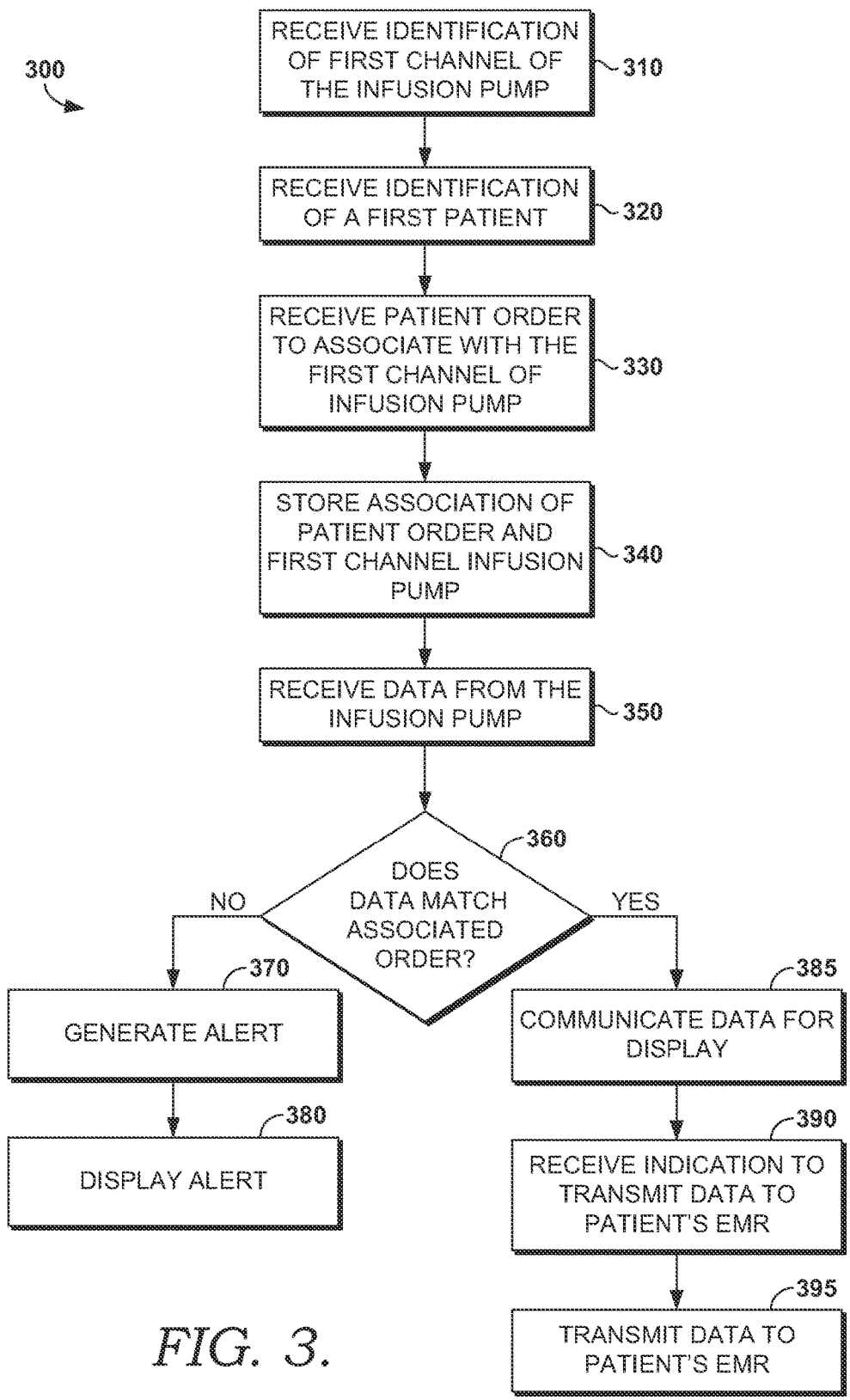

Turning now to FIG. 3, an illustrative flow diagram 300 is shown of a method for associating a patient order and a channel of a multi-channel infusion pump. Initially, an identification of a first infusion pump is received is received at step 310. An identification of an infusion pump may be received by scanning a bar code corresponding to the infusion pump, entering an identification of the infusion pump into the computing device, or searching for an infusion pump in a database. At step 320, an identification of a patient is received. The identification of the patient may be received in accordance with one of the methods described above, or any other method that allows for identification. At step 330, an identification of an order associated with a patient is received. Again, a patient order may be identified by any of the methods described above. In response to receiving identification of a channel of a multi-channel infusion pump and a patient order, the channel and the patient order are associated with one another and stored at step 340.

A continuous data feed from the infusion pump is received at 350. Data may be received continually from a first time to a second time. In one embodiment, the first time occurred upon initial association of the order to the channel of the infusion pump, and the second time occurred upon termination of the association of the order and a first channel of the infusion pump.

In one embodiment, a second channel of the infusion pump is identified and associated with a second order different from the first order for the patient. Again, this association of the second channel of the infusion pump and the second order is stored for the patient. As such, each channel of an infusion pump may be associated with a different order for the patient.

At step 360, it is determined whether the data received from the infusion pump for the first channel matches that of the first associated order. If the data does not match at step 360, an alert is generated at step 370. At step 380, the alert is displayed on a clinician device, such as clinical user device 226. If at step 360, it is determined that the data received from the infusion pump or the first channel matches that of the associated first patient order at step 385, the data from the infusion pump is communicated at step 385. The data received from the infusion pump is communicated to a user device for display. At step 390, an indication from the user verifying the data received from the infusion pump is received and at step 395, the data is transmitted and stored in the patient's electronic medical record.

Figures 4, 5:
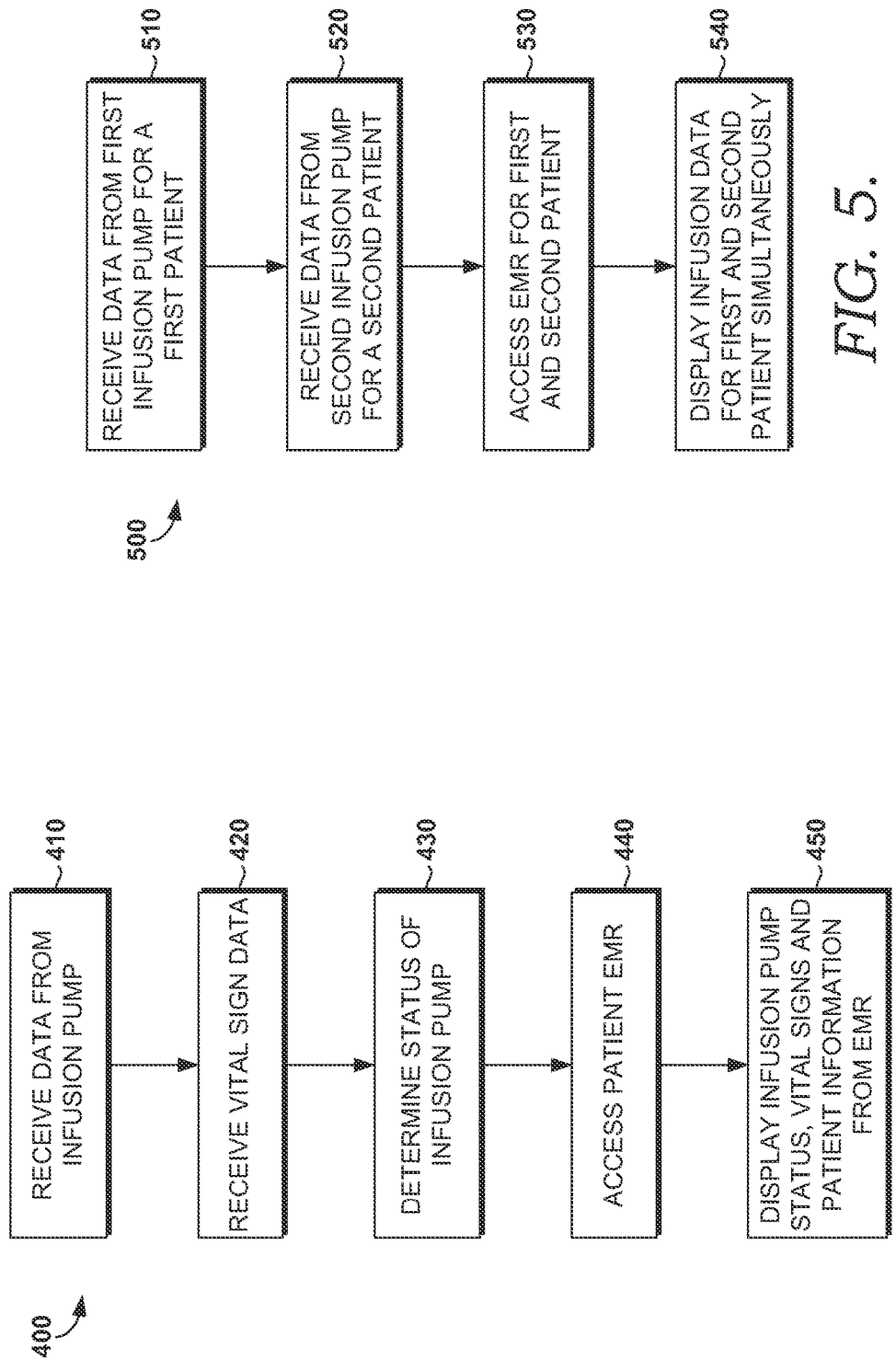

Turning now to FIG. 4, an illustrative flow diagram 400 is shown of a method for displaying infusion pump status, vital signs for a patient and patient information from the patient's electronic medical record, in accordance with an embodiment of the present invention. At step 410, data is received from an infusion pump connected to a patient. At step 420, vital sign data from a medical device connected to the same patient is received. At step 430, the status of the infusion pump is determined. For example, device status component 238 may determine whether a device is connected, has been stopped, and/or the rate and volume of the current infusion.

At step 440, the patient's electronic medical record is accessed for patient information. At step 450, the infusion pump status, vital sign information received and patient information from the EMR are displayed simultaneously on a graphical user interface such as the graphical user interface shown in FIG. 8 which will be described in more detail below.

Referring next to FIG. 5, an illustrative flow diagram 500 is shown as a method for displaying infusion data for a first and second patient simultaneously. Initially, data from a first infusion pump for a first patient is received at step 510. The data may include such information as rate of infusion, volume infused, and volume remaining. The data may further include alerts regarding the infusion pump data. At step 520, data is received from a second infusion pump for a second patient. The second patient is different from the first patient. The first infusion pump has been previously associated with a first order for the first patient as described in FIG. 3. The second infusion pump has been associated with an order for the second patient, again, as described in FIG. 3.

At step 530, the patient's electronic medical record for the first and second patient is accessed for patient information. At step 540, infusion data for the first and second patient is displayed simultaneously in a graphical user interface such as that shown in FIG. 11 and will be discussed in further detail below.

Figure 6:
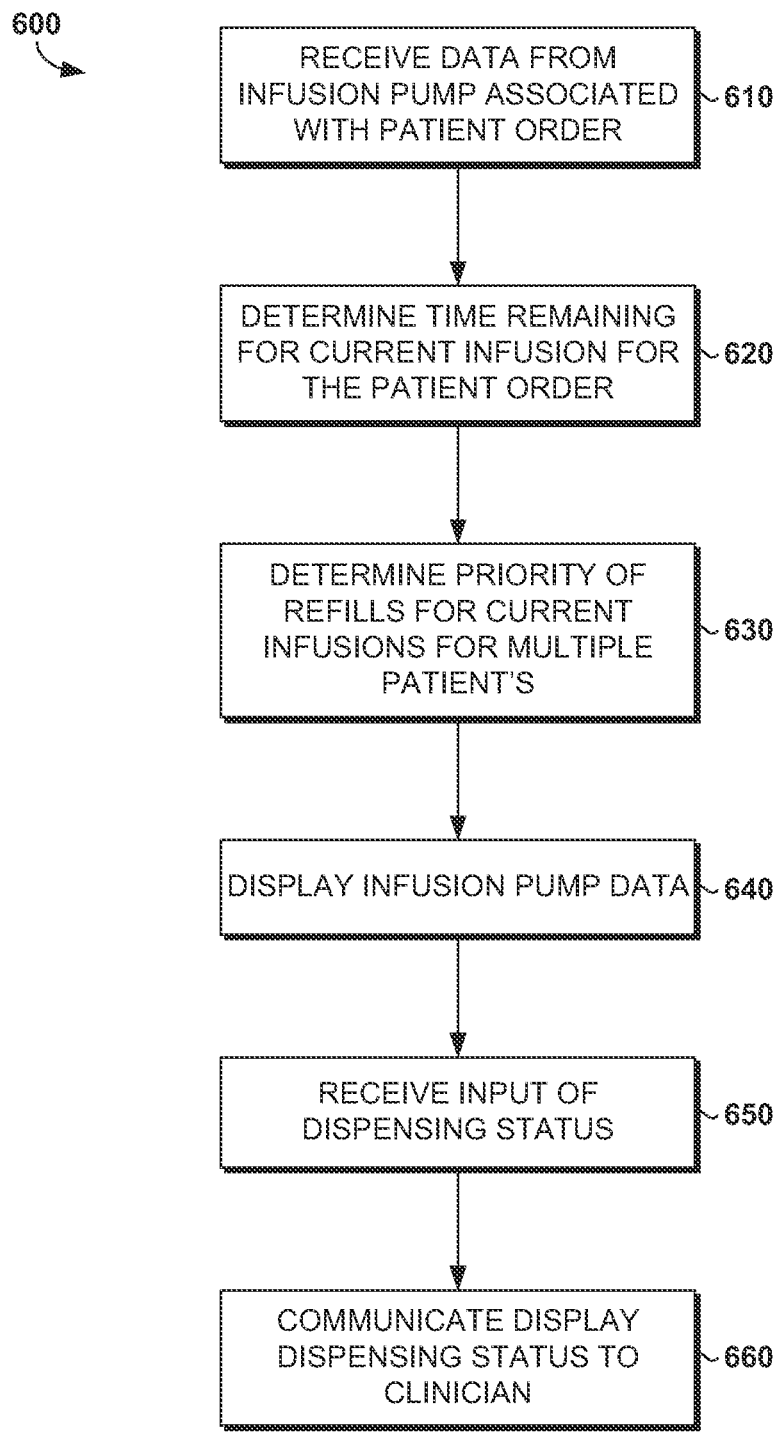

Referring next to FIG. 6, an illustrative flow diagram 600 is shown of a method for receiving input of dispensing status from a pharmacy application and communicating the dispensing status to a clinician. Initially, at step 610, data is received from an infusion pump that has been associated with a patient order. At step 620, the time remaining for the current infusion for the patient order is determined. The time remaining for the current infusion may be determined by the infusion time determining component 242. As described above, a variety of information may be utilized to determine the time remaining infusion fluid to be infused. The information used may include the rates that the rate of infusion, the remaining volume, expiration time of the infusion fluid and the like.

At step 630, the priority of pharmacy refills for current infusion for multiple patients is determined as described above with respect to pharmacy time remaining component 242. The priority of refills in the pharmacy can be determined by the time remaining for the current infusion, the lead time to prepare a replacement infusion, and the number of infusion fluid containers for the particular type of infusion that have already been completed and are in inventory.

At step 640, the infusion pump data received for multiple patients is displayed to a pharmacist. The infusion pump data may be displayed in priority of the highest priority to be completed to the lowest priority to be completed. An exemplary graphical user interface of a multiple patient infusion data view in the pharmacy is shown in FIG. 13.

Turning now to FIG. 7, an illustrative graphical user interface 700 is shown for a patient and plurality of orders and infusion pumps, in accordance with an embodiment of the present invention. Different channels of a multi-channel infusion pumps are capable of being associated with orders for a patient. An exemplary order 715 may be given to a patient of 1000 mL of dextrose 5% with 0.3% NaCl. The type of order may vary depending on the type of infusion pump that is required to carry out the order.

A patient identification area 705 identifies the patient, and gives other information regarding the patient, such as patient name, birth date, gender, age, and the like. An infusion pump channel identification area 710 identifies a channel of an infusion pump, and may also provide information about the channel and the infusion pump. In this example there are two channels 710 and 720 for a single infusion pump. There is one connected channel 710 associated with an order 715 for the patient. There is one channel 720 that has not been associated with an order. There is one medication order 725 that has not been associated with a channel of an infusion pump. Channels 710 and 720 each have a checkbox which may be selected to associate or disassociate a channel of an infusion pump. If an order is not currently associated, it may be selected to be associated with a suggested order. For example, channel 2 of device 1 720 may be associated with the propofol 725 medication order. The checkbox for channel 2 of device 1 720 and the propofol order 725 may be selected and associated by selecting associate button 730. Channel 1 of device 1 710 may be selected to disassociate it from the associated order 715. This may be done by selecting disassociate button 735. If there is an association made between an order and a channel of an infusion pump, the start and end time will be kept in the system for the patient, and most or all inaccuracies will disappear.

FIG. 8 is an illustrative graphical user interface 800 showing infusion data for a selected patient, in accordance with an embodiment of the present invention. A patient identification area 805 allows for the identification of a patient including, but not limited to, the patient's name, date of birth, gender, age, and an identification number or code. Infusion status area 805 indicates the connected infusion pump and channels. Here, there are five infusion pumps and channels connected that have been associated with orders for the patient. Associated orders include dopamine 810, insulin 815, norepinephrine 820, milrinone 825, and propofol 830. Information for each order includes the order information, the current rate of the infusion pump for the order, and any dispensing information. Each order further has an icon indicating the volume remaining for the infusion. Graphical user interface 800 further includes vital signs areas 835 and 840 for respiratory and blood pressure, respectively. In addition, infusion graphing area 860 includes infused volumes over time of milrinone 845, norepinephrine 850, and dopamine 855.

FIG. 9 is an illustrative graphical user interface 900 of a dialogue box indicating that an order currently associated to a pump channel does not match the latest version of the order. This type of box may appear if the order compatibility component 239 determines that the order associated with a pump channel is not current. The box indicates that there has been an order modification 905 for a patient. The box includes an alerting icon 910 stating that the most current version of the order has not been associated with the pump channel for the patient. The box includes an area of the currently associated version of the order 915 and the latest version of the order 920. A user, such as a clinician, may select the latest version button to associate the pump channel with the latest version of the order for the patient.

FIG. 10 is a graphical user interface 1000 depicting infusion information for multiple patients. In the exemplary graphical user interface multiple patient infusion information is included for Unit No. 1 1005. The graphical user interface includes patient identifying information 1010 and associated infusion orders that have been associated with infusion pumps and/or channels 1115. The graphical user interface also includes alerting icons 1120 depicting which patients have infusion alerts.

Figure 11:

Turning to FIG. 11, graphical user interface 1100 depicting multiple patients for Unit 1 1105 is shown. The multi-unit view shows that patient Thomas Walker 1110 has an associated infusion pump or channel 1115 that currently is not communicating any data. As such, it is displayed that the pump for the particular order has no data to display.

Figure 12:
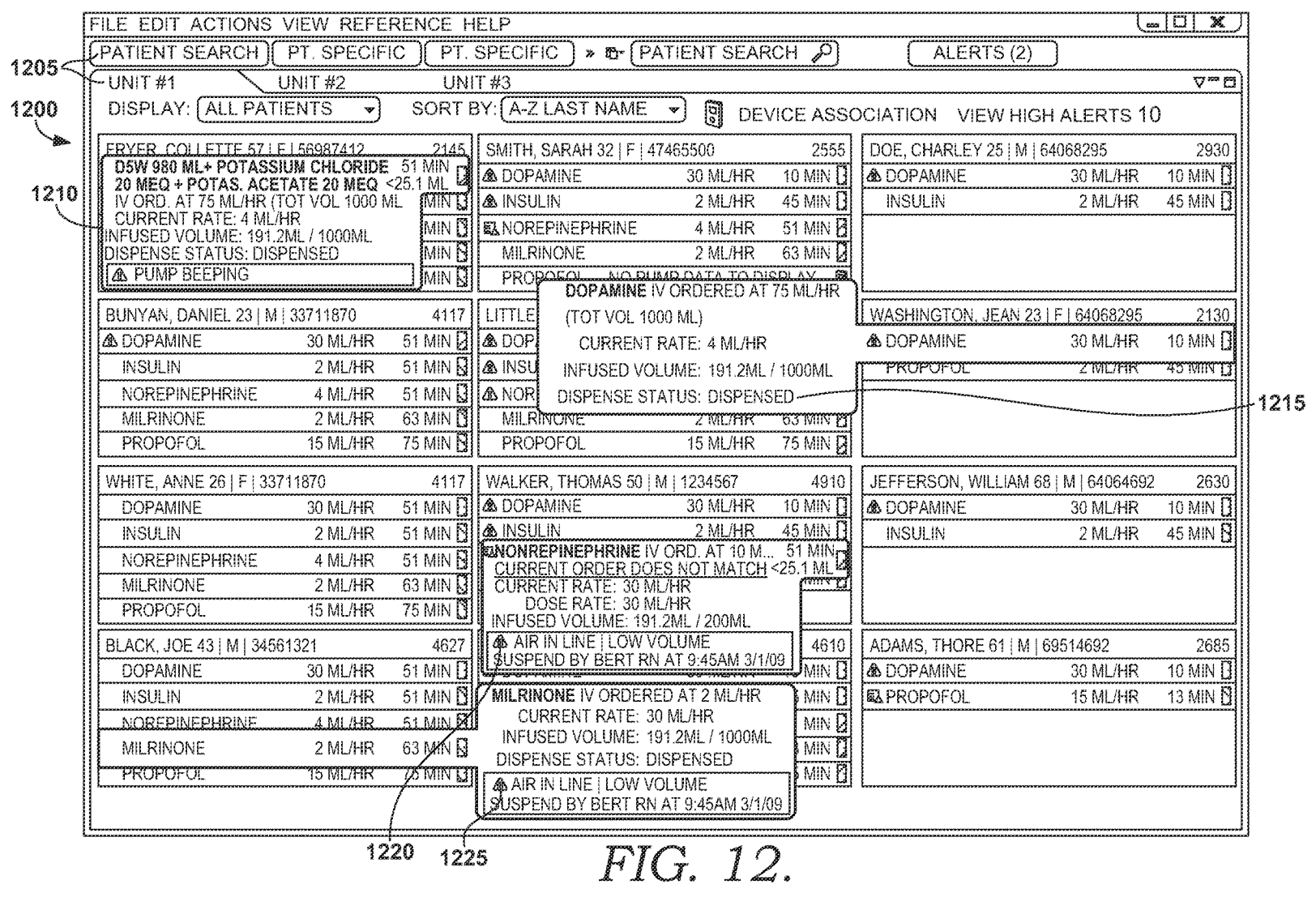

Turning to FIG. 12, an illustrative graphical user interface 1200 of a multi-patient view of infusion data is shown. Again, multiple patients for Unit 1 1205 and their infusion data are shown. In addition, alerts and additional information regarding the alerts are depicted. When a user hovers over an order listed for a patient or alert icon, an additional box appears with more information regarding the order and the alert. For example, box 1210 shows that the pump associated with patient Collette Fryer's potassium chloride order is beeping. The additional information box 1210 also includes the current rates of the infusion, the amount of volume that has been infused, and the dispensing status, along with details of the original order. Textbox 1215 displays details for the dopamine order for patient Jean Washington. It also includes the current rate of infusion received from the infusion pump, along with the volume that has been infused. The textbox also includes the dispensing status from the pharmacy regarding whether a new bag or container of infusion fluid has been dispensed.

Box 1220 depicts that the pump associated with the norepinephrine order for Thomas Walker is sending an alert that there is air in the line of the pump. Further, it shows that this alert has been suspended by a nurse who has gone to examine the pump. It includes the time of suspension of the alert by the nurse. Box 1225 also shows an alert depicting that there is air in the line of the infusion pump associated with the milrinone order. To prevent the pharmacist or automated pharmacy system from duplicating the replace/refill of the infusion. Automated pharmacy system may automatically update the dispense status.

Referring to FIG. 13, a continuous data feed is received from at least one device operable to assist in treating a patient 1310. Such a device may be in various embodiments, an infusion pump, a medical device, or a combination thereof. A selected protocol is then received for the patient 1320. After a time range for the selected protocol is received 1330, data is displayed from at least one device according to the selected protocol for the selected time range 1340.

Referring next to FIG. 14, an illustrative graphical user interface 1400 is shown of a pharmacy view of infusion data received from infusion pumps. The interface 1400 includes various types of information relating to multiple devices and channels for multiple patients in health care facility. The types of information include the patient name or identification number, the patient location 1415, the ingredient of the infusion order 1420, the type of infusion 1425, the total volume to be infused for the order 1430, the rate of infusion received from the infusion pump 1435, the amount of fluid of the order that has been infused 1440, the amount of fluid remaining to be infused 1445, and the calculated time remaining of the infusion 1450. Further, alerts 1410 received from the infusion pump indicating that the volume is low or some other type of alert are displayed. In addition, an interactive area regarding the dispensing status 1455 of a replacement or refill for an infusion order is provided. In addition, if a clinician or nurse has placed a request for a refill from a clinician device, this may also be displayed to the pharmacists to prevent the pharmacist or automated pharmacy system from duplicating the replace/refill of the infusion.

A pharmacist or technician in the pharmacy may indicate the status of the replacement or refill of infusion fluid. These statuses include that the replacement infusion has been delivered 1475, that the delivery is in process 1480, the infusion has been dispensed but yet to begin delivery 1485, that the dispensing is in process 1490 or the replacement/refill infusion is being prepared. In some instances, such with an automatic pharmacy dispensing system, the status of the replacement or refill infusion can be updated automatically upon dispensing. This indication allows for pharmacy users to know the status of infusion orders to be filled by the pharmacy and adjust the workflow accordingly. In other words, if an infusion replacement has been dispensed or delivered, there is no need for another technician to fulfill the order. However, if no status is indicated, then the pharmacy user knows to begin dispensing.

That replacement/refill infusion status indication for a patient order can be communicated to a clinician, such as a nurse. This allows the nurse to see the status of the replacement/refill of the pharmacy without having to directly contact the pharmacy to check status.

The pharmacy infusion orders for the patients are displayed in order of time remaining for the existing infusion. For example, patients with the lowest calculated time remaining for their current infusion are displayed at the top of the graphical user interface 1400 and patients with the most calculated time remaining for need of a replacement infusion are displayed at the bottom. Icons indicating that the rates of an infusion are increasing 1465 or decreasing 1470 are also displayed so that a pharmacist can see if a particular infusion may need to be replaced sooner than the calculated time remaining for the current infusion.

Referring back to FIG. 15, it may be desirable for a clinician to select a protocol corresponding to a specific time interval 1520, rather than a treatment, for receiving data associated with the patient. For example, in one embodiment, a clinician may desire to display and review data every 15 minutes for a selected range of time. In another embodiment, the clinician may prefer to select a protocol that is predetermined by the hospital or health care facility. Predetermined intervals 1530 appear, in one embodiment, in a drop-down box. In this example, the predetermined intervals appear as "Protocol 1" and "Post Surgery". As discussed above, the clinician may select a protocol corresponding to a specific treatment or order, such as "Post Cardiac Catheterization" (not shown).

Referring to FIG. 16, a clinician may desire to further customize a view of the data. In such a scenario, the clinician may select a subset of the time range within the selected protocol. Once the desired subset is selected, the clinician may increase or decrease the interval associated with that subset. In one embodiment, a collapse or expand button appears within a user interface. In another embodiment, the clinician may simply select a protocol corresponding to a specific time interval, discussed above, for the subset of the time range.

If multiple data entries are available within a single cell, either after increasing the interval (i.e. collapsing columns) or because the user device communication component determined that multiple data entries should be available, such as for an unexpected or extreme reading, a range of data 1610 for that subset, in one embodiment, is presented to the user. In another embodiment, the range of data 1610 represents a range of data for the preceding interval to the present interval.

In practice, and referring back to FIG. 14, a clinician may desire to select a protocol for a particular patient, Walker T 1495 (also referred to as Thomas Walker). Assuming Thomas Walker 1495 is selected, the screenshot represented by FIG. 15 appears. The infusion documentation 1540 may comprise, in this example and for this particular protocol, vital signs 1542, hemodynamics 1544, continuous infusions 1546, and medication infusions 1548. Continuous infusions 1546 may further comprise, in this example, dopamine 1551, insulin 1552, dobutamine 1553, dextrose 0.5% in water 1554, TPN 1555, and heparin flush 1556. Medication infusions 1548 may further comprise, in this example, ampicillin 1557. Time intervals 1560, 1562, 1564, 1566, 1570, 1572, 1574, 1576, 1580, 1582, 1584, 1586 are fifteen minute intervals, for a three hour period immediately after surgery. According to the protocol, after the initial three hour time period, the intervals become longer. For example, time interval 1590 is a two hour interval and time intervals 1592, 1594, 1596 are each one hour intervals. In other embodiments, directed to different protocols, the time intervals are tailored to the requirements of the protocol. If a specific time range 1500 is selected, in this example 11:00-13:00 and 140:00-16:00, the screenshot of FIG. 16 appears. As described above, in this view a practitioner is presented with ranges of data associated with the selected time range or time ranges.

Figure 20:

In another embodiment, referring to FIG. 20, multiple data entries may appear as staggered within a single cell 2010 such that it is apparent to a clinician that multiple data entries exist for the approximate time embodied by the single cell (because the actual time for the data entry may not correspond precisely with the time displayed on the select column; rather, the data entry may be in between an interval of times as labeled by two columns; i.e. an interval may be 30 minutes, with two columns in the interval labeled 10:30 and 11:00, but a data entry may exist at 10:32; thus, the approximate time for that entry is 10:30). A single value appears face up, with the remaining values hidden.

Figure 21:
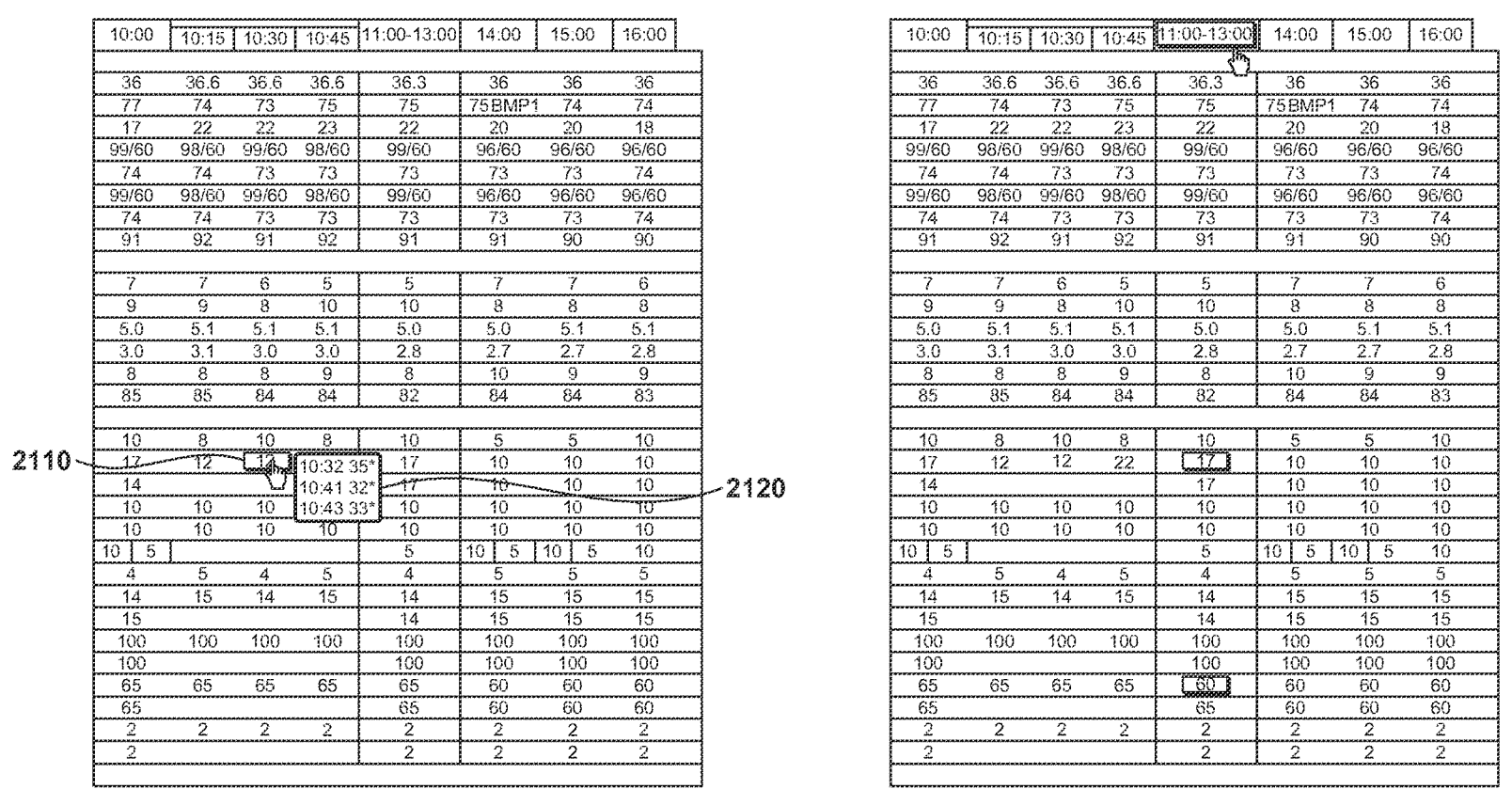

Referring to FIG. 21, a clinician may position a cursor, in one embodiment, to hover over the single cell 2110, thereby displaying all values 2120 associated with the approximate time represented by the single cell, in addition to the actual point in time the data was received. The clinician may desire to expand the display, so that each actual point in time is represented by its own column, thereby giving each data entry its own individual cell and providing greater detail and clarity to the display. In one embodiment, this is accomplished by double-clicking the staggered cell.

Figure 17:
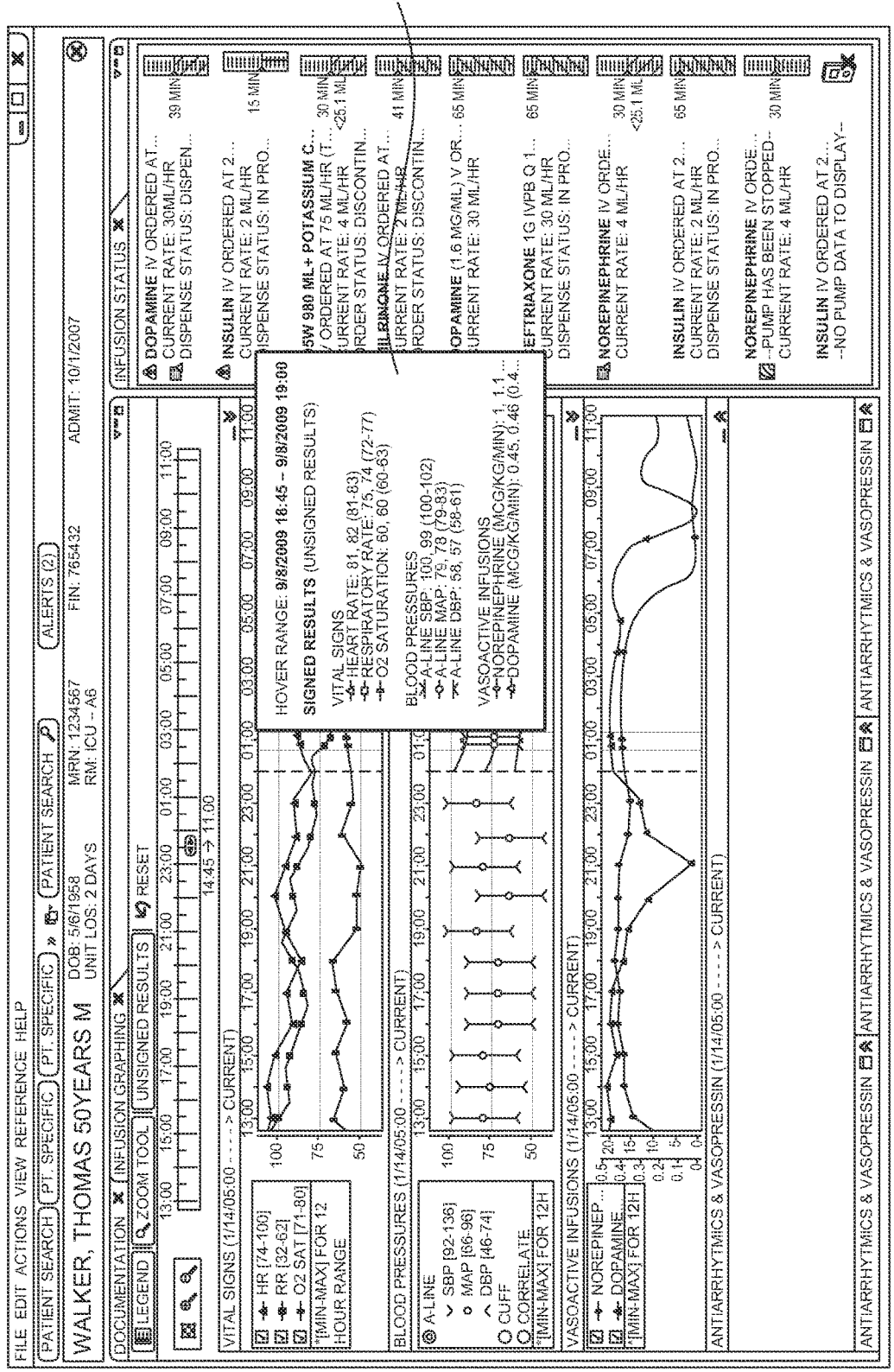

Referring to FIG. 17, in one embodiment, the data is presented in a graphical format. A clinician may position the cursor, in one embodiment, to hover over a portion of the graph, presenting a data box 1710 to the clinician containing a range of data available for the selected time range. An indication of whether the data is signed or unsigned is readily apparent to the clinician. In one embodiment, signed results appear as boldfaced text, while unsigned results appear as normal text.

Figure 18:
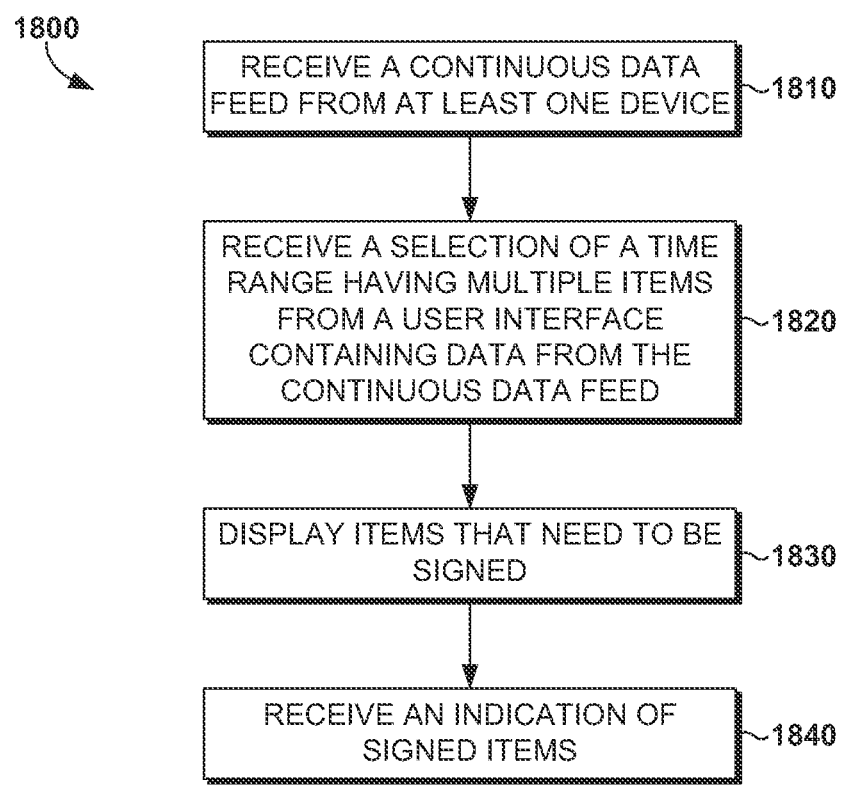
FIG. 18 is a flow diagram of a method in accordance with an embodiment of the present invention.

Referring to FIG. 18, a continuous data feed is received from at least one device operable to assist in treating a patient 1810. A time range is selected via a user interface having multiple items containing data from the continuous data feed 1820. Items that need to be signed are displayed 1830 and an indication that the items have been signed is received 1840.

Figure 19:
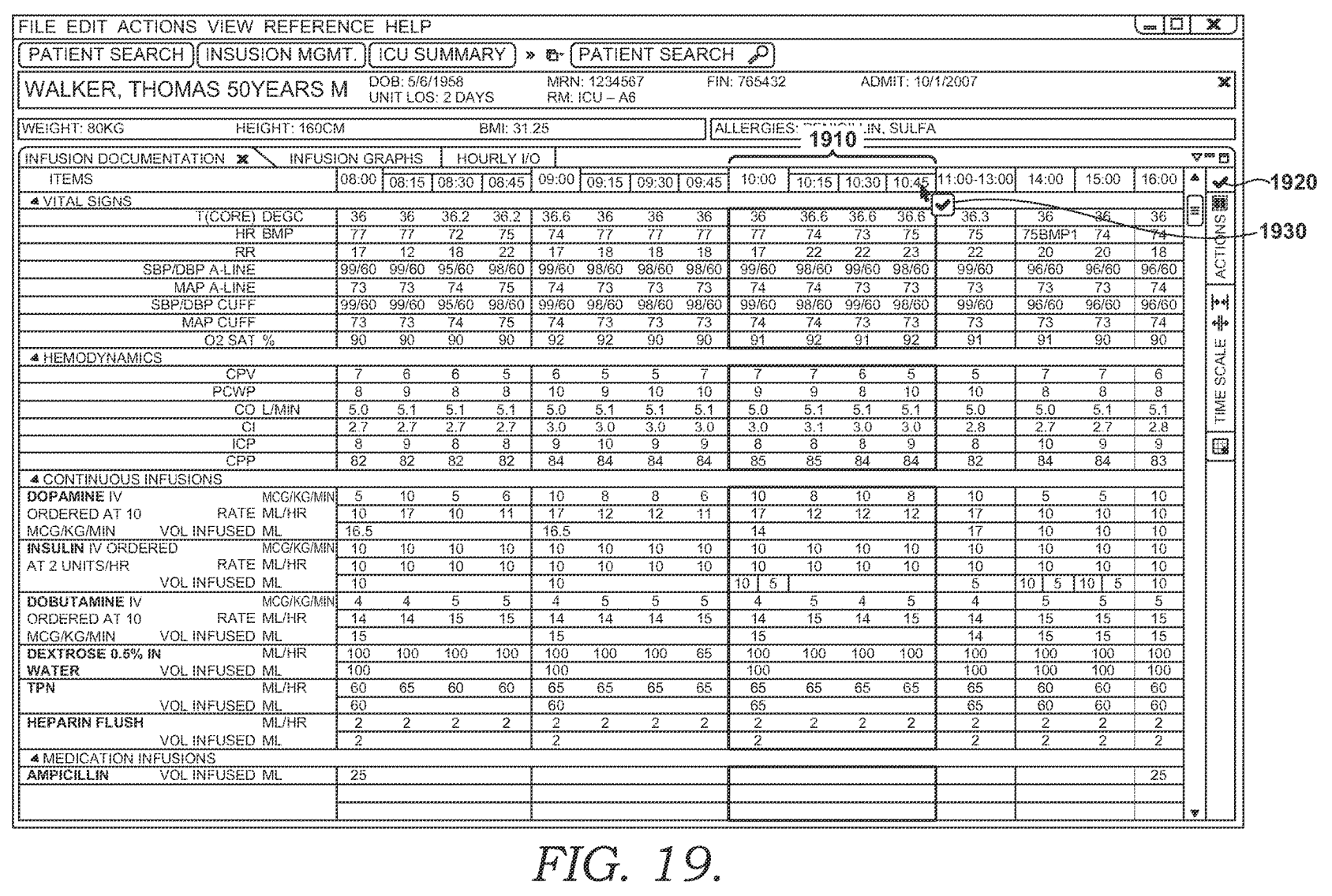

Referring to FIG. 19, after a time range 1910 is selected, a sign button may be activated or clicked. In one embodiment, a sign button appears to hover 1930 next to the selected time range if items within the time range require review. In another embodiment, a sign button is fixed 1920 within the user interface. Once the sign button is clicked, items that need to be signed are presented to the clinician. Prior to signing the data, it may be necessary for a clinician to edit or enter additional data. In one embodiment, all items that require review appear in a single sign box, allowing the clinician to review the data and click a single sign button within the single sign box. This causes each item to be signed so the data may be transmitted to and stored in the patient's EMR.

If no additional information is required, an indication that the items have been signed is received. Referring to FIG. 20, a cell with signed data 2010 is shown face up, and presented in boldfaced text to distinguish it from a cell with unsigned data 2020. Each of the cells, 2010 and 2020 in FIG. 20, appear as staggered cells, denoting that hidden values are available as discussed above.

Figure 22:
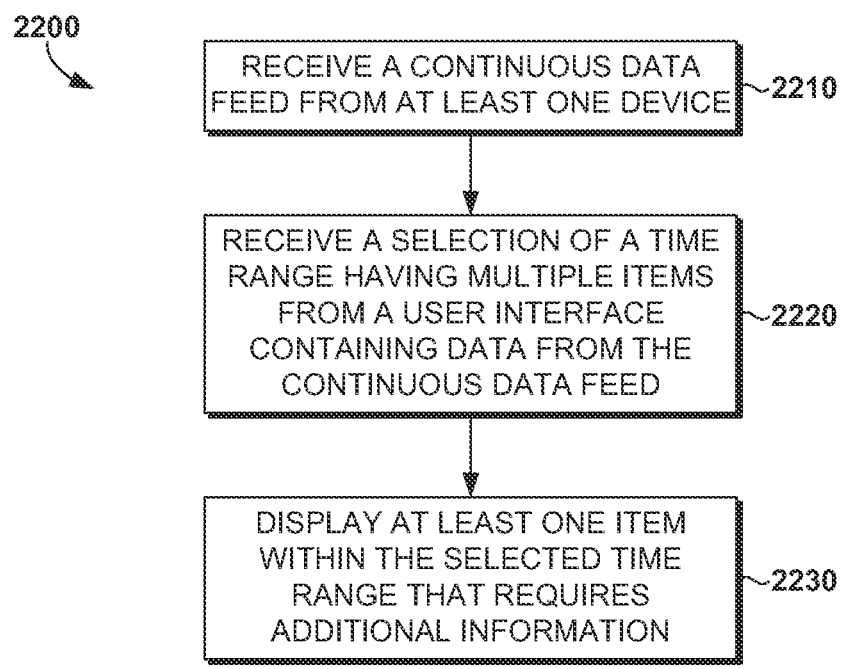
FIG. 22 is a flow diagram of a method in accordance with an embodiment of the present invention.

If additional information is required, control passes to the action component. Referring to FIG. 22, a continuous data feed is received from at least one device operable to assist in treating a patient 2210. A time range is selected via a user interface having multiple items containing data from the continuous data feed 2220. Items are then displayed that require additional information 2230 from a clinician.

Figure 23A:
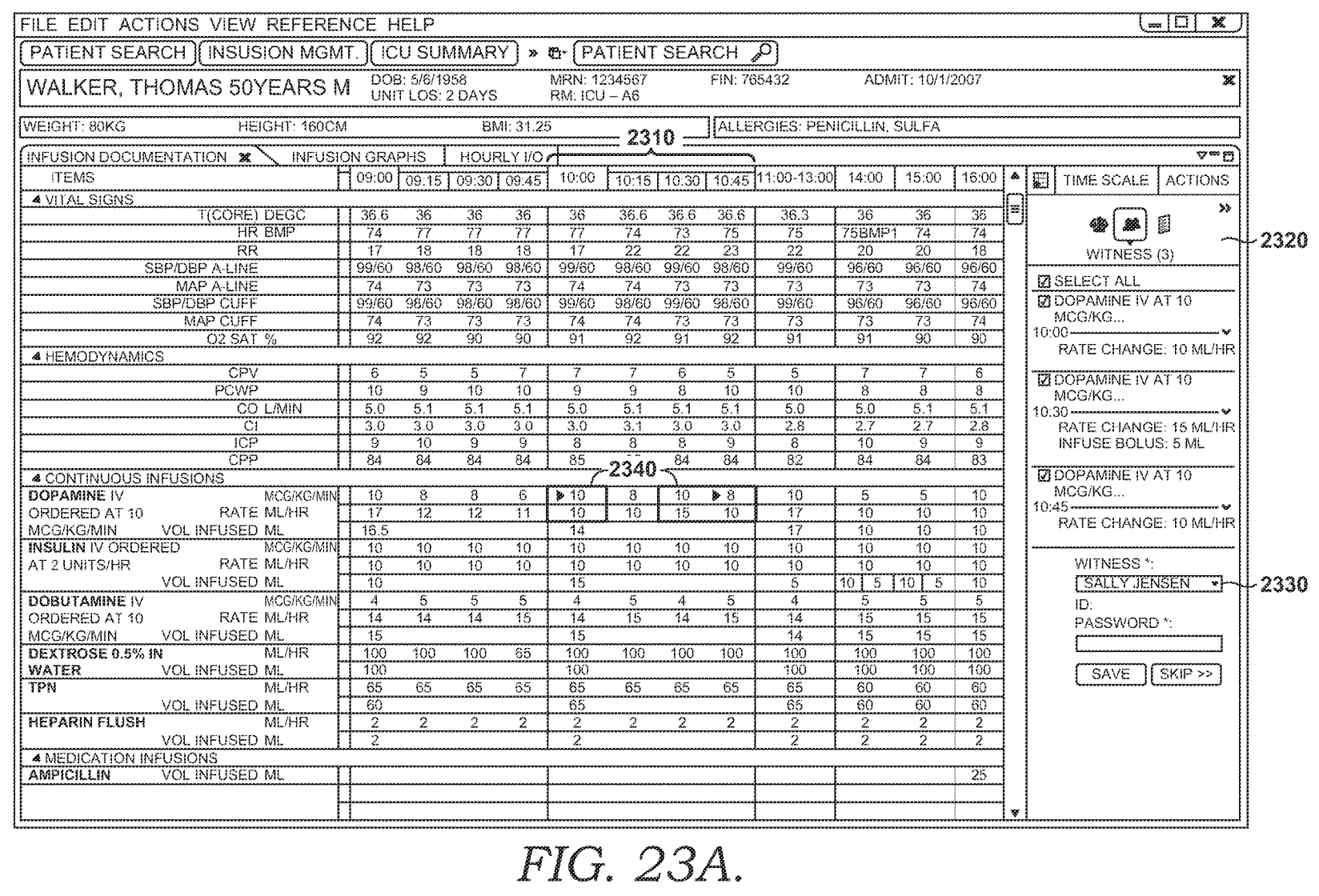
Figure 23B:
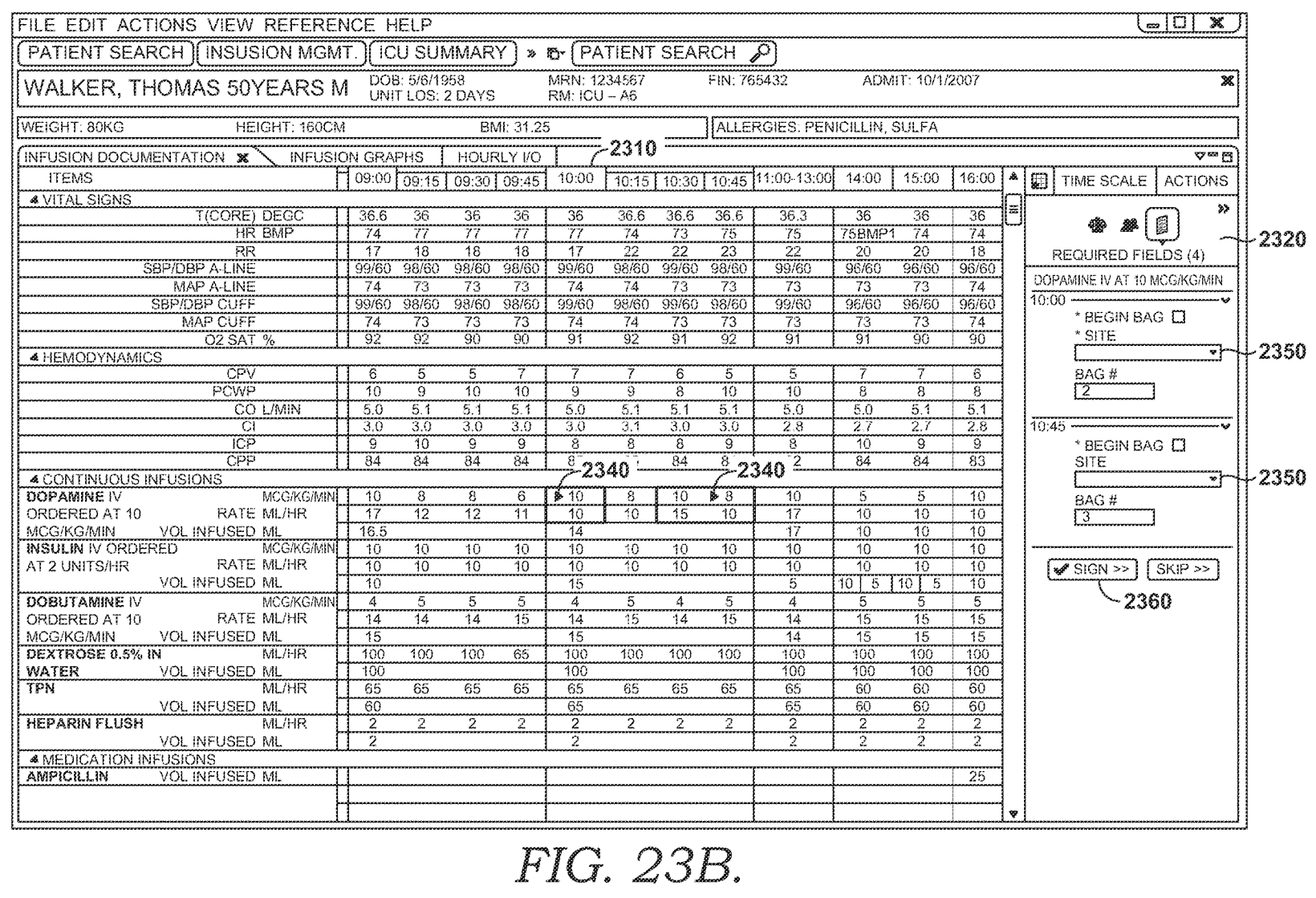

Referring to FIGS. 23a and 23b, a clinician may select a time range 2310. In this example, the clinician has selected 10:00-11:00. An action box 2320 appears, in one embodiment, in the right-hand column, listing each item that requires additional information. In another embodiment, an action box may hover next to the selected time range. In this example, a witness name 2330 is required for each of three infusions. Once the witness name is entered, the information can be saved. However, it may be necessary to add additional information. For example, a dopamine infusion may also require information pertaining to a specific site of administration 2350 on the patient. In another embodiment, it may be necessary to enter a patient's weight. Once the required additional information is entered, the items may be signed by clicking the sign box 2360. It may also be apparent to a clinician which items require additional information because the individual cells pertaining to these items may include, in one embodiment, a symbol 2340 or special appearance causing them to stand out from items which do not require additional information.

Figure 24:

Referring to FIG. 24, when the cursor is positioned over a cell that requires additional information, a hover box 2410 appears, in one embodiment, indicating what additional information is required. In this example, when the cursor is positioned over the rate of dopamine at 14:00, a hover box appears indicating that the site of administration is required.

Many different arrangements of the various components depicted, as well as components not shown, are possible without departing from the scope of the claims below. Embodiments of our technology have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

The invention claimed is:

1. One or more non-transitory computer storage media having computer-executable instructions embodied thereon, that when executed, perform a method for indicating an action is required for an item associated with infusion documentation, the method comprising:
    receiving a first continuous data feed from a first device operable to assist in treating a patient;
    receiving a second continuous data feed from a second device operable to assist in treating the patient;
    receiving a selection of a time range having multiple items from a user interface containing data from the first continuous data feed and the second continuous data feed;
    identifying a plurality of items within the selected time range that each requires additional information from a clinician based on data received from the first continuous data feed and the second continuous data feed, each item being associated with one of the first device or the second device;
    identifying the additional information required for the plurality of items; and
    displaying an action box for entering the additional information for items associated with the first device and the second device, the action box listing each item that requires additional information and indicating what additional information is required, wherein the action box is configured to receive input associated with the additional information for each item.

2. The media of claim 1, wherein the additional information required for at least one item is a witness name.

3. The media of claim 1, wherein the additional information required for at least one item is a site associated with intravenous therapy.

4. The media of claim 1, wherein the additional information required for at least one item is a weight associated with the patient.

5. The media of claim 1, further comprising presenting the clinician with a selectable button that, when activated after entering the additional information, indicates that the data is ready to be transmitted or published to an EMR associated with the patient.

6. The media of claim 5, wherein the selectable button appears as a hover box next to a selected time range.

7. A computerized system for entering additional information associated with infusion documentation, the system comprising:
    a first medical device comprising computer readable media transmitting data associated with a patient;
    a second medical device comprising computer readable media transmitting data associated with the patient;
    a computing device remote from the first medical device and the second medical device, the computing device having one or more processors and one or more computer-readable media with computer-readable instructions for executing a method comprising:
        receiving a first continuous stream of data from the first medical device;
        receiving a second continuous stream of data from the second medical device;
        receiving a selection of a time range associated with the first continuous stream of data and the second continuous stream of data;
        determining more than one item of data requires additional information within the selected time range, the more than one item of data comprising a first item the associated with the first continuous stream of data and a second item associated with the second continuous stream of data; and
        providing a graphic user interface component comprising an action box for entering additional information for the first item associated with the first continuous data stream and the second item associated with the second continuous data stream, the action box listing each item that requires additional information and indicating what additional information is required, wherein the action box is configured to receive input associated with the additional information for each item.

8. The system of claim 7, wherein the graphic user interface component is presented to a user via a user device.

9. The system of claim 8, wherein the user device is remote from the computing device.

10. The system of claim 7, wherein the first medical device is a first infusion pump administering a first infusion and the second medical device is a second infusion pump administering a second infusion.

* * * * *

UNITED STATES PATENT AND TRADEMARK OFFICE
CERTIFICATE OF CORRECTION

PATENT NO. : 9,927,943 B2
APPLICATION NO. : 12/890326
DATED : March 27, 2018
INVENTOR(S) : Mary Gannon Page 1 of 1

It is certified that error appears in the above-identified patent and that said Letters Patent is hereby corrected as shown below:

In the Claims

Column 22, Line 26, Claim 7: Please remove "first item the" and replace with --first item--.

Signed and Sealed this
Second Day of October, 2018

Andrei Iancu
*Director of the United States Patent and Trademark Office*